(12) United States Patent
Ciccarelli et al.

(10) Patent No.: US 12,201,847 B2
(45) Date of Patent: Jan. 21, 2025

(54) SYSTEMS AND METHODS TO PROVIDE CIRCADIAN IMPACT

(71) Applicant: ABL IP Holding LLC, Atlanta, GA (US)

(72) Inventors: David P. Ciccarelli, Johns Creek, GA (US); Daniel Aaron Weiss, Tucker, GA (US); Benjamin Marshall Suttles, McDonough, GA (US)

(73) Assignee: ABL IP Holding LLC, Atlanta, GA (US)

( * ) Notice: Subject to any disclaimer, the term of this patent is extended or adjusted under 35 U.S.C. 154(b) by 142 days.

(21) Appl. No.: 15/971,107

(22) Filed: May 4, 2018

(65) Prior Publication Data
US 2018/0318601 A1    Nov. 8, 2018

Related U.S. Application Data

(60) Provisional application No. 62/502,027, filed on May 5, 2017.

(51) Int. Cl.
*A61N 5/00*    (2006.01)
*A61M 21/02*   (2006.01)
(Continued)

(52) U.S. Cl.
CPC .......... *A61N 5/0618* (2013.01); *A61M 21/02* (2013.01); *A61M 2021/0044* (2013.01); *A61N 2005/0663* (2013.01); *A61N 2005/0667* (2013.01)

(58) Field of Classification Search
CPC ............................. A61N 5/0618; A61M 21/02
See application file for complete search history.

(56) References Cited

U.S. PATENT DOCUMENTS 4,922,930 A    5/1990 Adkins et al.
5,143,065 A    9/1992 Adkins et al.
(Continued)

FOREIGN PATENT DOCUMENTS

CA    3017104    9/2016
WO    2016145059 A1    9/2016

OTHER PUBLICATIONS

U.S. Appl. No. 15/971,145, Final Office Action, Mailed On Dec. 23, 2020, 20 pages.
(Continued)

*Primary Examiner* — Sana Sahand
(74) *Attorney, Agent, or Firm* — Kilpatrick Townsend & Stockton LLP

(57) ABSTRACT

Certain examples involve a circadian effect light fixture. The circadian effect light fixture includes a controller to receive a modifying factor based on a circadian impact profile. The modifying factor includes an indication of an intensity value, a correlated color temperature value, and a color value over a range of time. The circadian effect light fixture also includes a first lighting element controlled by the controller to produce a first light output having a first intensity, a first correlated color temperature, and a first color value. Further, the circadian effect light fixture includes a second lighting element controlled by the controller to produce a second light output having a second intensity, a second correlated color temperature, and a second color value. A combined light output of the first lighting element and the second lighting element tracks the modifying factor over the range of time.

10 Claims, 15 Drawing Sheets

(51) Int. Cl.
*A61N 5/06* (2006.01)
*A61M 21/00* (2006.01)

(56) References Cited

U.S. PATENT DOCUMENTS

| | | | | |
|---|---|---|---|---|
| 5,721,471 A | * | 2/1998 | Begemann | H05B 47/10 |
| | | | | 250/214 AL |
| 7,408,887 B2 | | 8/2008 | Sengupta et al. | |
| 7,706,884 B2 | | 4/2010 | Libbus | |
| 9,163,983 B2 | | 10/2015 | Olds et al. | |
| 9,220,202 B2 | | 12/2015 | Maxik et al. | |
| 10,022,556 B1 | * | 7/2018 | Holbert | H05B 45/37 |
| 2003/0069616 A1 | * | 4/2003 | Skene | A61M 21/00 |
| | | | | 607/88 |
| 2003/0231495 A1 | * | 12/2003 | Searfoss, III | A61M 21/00 |
| | | | | 362/249.12 |
| 2009/0240311 A1 | * | 9/2009 | Andersen | A61M 21/00 |
| | | | | 607/90 |
| 2009/0326616 A1 | | 12/2009 | Aarts et al. | |
| 2011/0015495 A1 | | 1/2011 | Dothie et al. | |
| 2013/0119886 A1 | * | 5/2013 | Hurst | H05B 47/10 |
| | | | | 315/246 |
| 2013/0119891 A1 | * | 5/2013 | Herremans | H05B 47/16 |
| | | | | 315/293 |
| 2014/0052220 A1 | * | 2/2014 | Pedersen | A61M 21/00 |
| | | | | 607/88 |
| 2014/0375222 A1 | * | 12/2014 | Rains, Jr. | G01J 3/50 |
| | | | | 315/158 |
| 2015/0022093 A1 | | 1/2015 | Smith et al. | |
| 2015/0062892 A1 | * | 3/2015 | Krames | F21K 9/232 |
| | | | | 362/231 |
| 2015/0148871 A1 | * | 5/2015 | Maxik | G16H 20/70 |
| | | | | 607/88 |
| 2015/0186594 A1 | * | 7/2015 | Zhang | A61N 5/0618 |
| | | | | 703/2 |
| 2015/0234207 A1 | | 8/2015 | Koifman | |
| 2015/0334808 A1 | | 11/2015 | Hack et al. | |
| 2015/0348468 A1 | | 12/2015 | Chen et al. | |
| 2015/0375008 A1 | | 12/2015 | Gretz et al. | |
| 2016/0034671 A1 | | 2/2016 | Hyde et al. | |
| 2016/0071393 A1 | | 3/2016 | Kaplan et al. | |
| 2016/0151012 A1 | | 6/2016 | Bozkurt et al. | |
| 2016/0158486 A1 | | 6/2016 | Colbaugh et al. | |
| 2016/0158487 A1 | | 6/2016 | Colbaugh et al. | |
| 2016/0158572 A1 | | 6/2016 | Nolan et al. | |
| 2016/0159276 A1 | | 6/2016 | Thomas et al. | |
| 2016/0199000 A1 | | 7/2016 | Gimenez et al. | |
| 2016/0381763 A1 | | 12/2016 | Loeb et al. | |
| 2017/0105265 A1 | * | 4/2017 | Sadwick | H05B 47/11 |
| 2017/0245354 A1 | * | 8/2017 | Yadav | H05B 45/20 |
| 2018/0177976 A1 | * | 6/2018 | Burstein | G02B 6/0011 |
| 2018/0339127 A1 | | 11/2018 | Van Reen et al. | |
| 2019/0209858 A1 | * | 7/2019 | Slaughter | A61N 5/0613 |

OTHER PUBLICATIONS

Canada Application No. 3,003,973, Office Action mailed on Jun. 12, 2019, 4 pages.
Canada Application No. 3,003,973, Office Action mailed on Jul. 7, 2021, 5 pages.
U.S. Appl. No. 15/971,145, Final Office Action, Mailed On Apr. 7, 2022, 24 pages.
Ca3176590, "Office Action", Jun. 6, 2024, 3 pages.

* cited by examiner

SYSTEMS AND METHODS TO PROVIDE CIRCADIAN IMPACT

CROSS-REFERENCE TO RELATED APPLICATION

This disclosure claims priority to U.S. Provisional Application No. 62/502,027 entitled "Systems and Methods to Provide Circadian Impact," filed May 5, 2017, the entirety of which is hereby incorporated by reference herein.

TECHNICAL FIELD

This disclosure relates generally to the field of determining and providing circadian factors in artificial light sources.

BACKGROUND

Circadian response in humans may be affected by the amount and color of light that is received by the eyes. Exposure of the eyes to different wavelengths of light may promote or suppress melatonin production, which in turn may promote or suppress sleep in humans, as well as impact other circadian hormones, including Cortisol levels and Alpha amylase levels. Other physiological biomarkers may also be impacted by light. The presence of blue light may promote wakefulness, while the presence of yellow light may negate the impact of the blue spectrum. In addition, exposure of the eyes to the different wavelengths may have different effects at different times of day. Exposure to bright light, or to moderate light in the blue spectrum, soon after waking may cause the person's circadian rhythm to advance, i.e., the person may fall asleep or awaken the following day earlier than otherwise. Exposure to bright light or moderately intense blue light shortly before going to bed may cause the circadian rhythm to delay, i.e., the person may fall asleep or awaken the following day later than otherwise. At either time of day, exposure to light in the yellow spectrum may negate the effects of the bright or blue-spectrum light.

The ability to adjust one's wakefulness finds use in the medical treatment of sleep disorders, adjusting to a new schedule (e.g., night shift workers or travelers between time zones), and in promoting one's own well-being. For certain medical conditions (including conditions other than sleep-related), a doctor may prescribe a certain type or amount of light treatment. It is desirable to have a circadian stimulus system capable of reliably producing an appropriate amount and spectrum of light, in order to achieve a user's desired circadian response. Existing systems may use a fixed light source to produce a certain intensity or color of light. However, normal changes in a person's exposure to light throughout the day may cause a fixed light source to produce an inappropriate type or amount of light.

SUMMARY

The implementations described herein may include one or more of a distributed circadian model, a background circadian strategy, or a circadian accent device.

A distributed circadian model may describe circadian stimuli or circadian impact experienced within a modeled space. The space that is modeled may be any area that receives light, and the model may include information about circadian impact (e.g., an intensity of light, a color or color temperature of light) occurring within the modeled space. The circadian factors may be related to ambient light in the modeled space, or to the output of light fixtures that produce light within the modeled space. In some cases, the circadian model may assign a value to the space, such as a value indicating a numeric or qualitative amount of circadian impact produced by the light within the modeled space.

The distributed circadian model may be updated based on additional information. For example, additional information may be received from sensors within the modeled space, from a lighting fixture having information about circadian factors of its produced light, from feedback provided by users of the space being modeled, from environmental sources (e.g., a weather report for the geographical region of the modeled space) from any other suitable source of information. The distributed circadian model may be used to calculate personal exposure to circadian impact. For example, an application running on a mobile device may receive data from the distributed circadian model to estimate the amount of circadian impact experienced by a user of the mobile device.

In addition, a circadian strategy may be implemented by a background circadian system ("BCS"), such as a remote computing server or a device installed on a lighting network. A circadian strategy may describe a desired level of circadian impact ("CI") over a period of time. CI includes circadian stimulus, equivalent melanopic lux (EML), or any other type of circadian metric. For example, a strategy intended to promote a regular sleeping schedule may describe a series of CI levels over a 24-hour period, such as high-intensity light with increased intensity in the blue spectrum in the morning and low-intensity light with decreased intensity in the blue spectrum in the evening. Alternatively, a strategy intended to promote wakefulness during an employee shift may describe CI levels over an 8-hour period, such as high-intensity light throughout the 8-hour period, with increased intensity of the blue spectrum in the first four hours and decreased intensity of the blue spectrum in the next four hours. The BCS may provide one or more profiles to a lighting network. A profile may include information describing a circadian strategy, such as colors, color temperatures, and/or levels of light intensity associated with time periods of the strategy. Alternatively, a profile may specify one or more CI values or other values. The BCS may implement the profile for one or more locations. Profiles may be implemented in one or more rooms, a building, a campus or neighborhood area (including indoor and/or outdoor spaces), a park, or any other suitable location.

In some implementations, a lighting network that receives information related to a profile may produce light output based on a combination of the profile and of the requested light output. For example, light fixtures in an office may produce light based on a combination of light intensity indicated by a profile implemented in the office and requests received from occupants of the office (e.g., dimming the lights for a presentation).

The requested light output may also request an adjustment to the output specified by the profile. For example, a user may request an increase or decrease in CI beyond what is provided by the profile. The request may be relative, may request a percentage adjustment, or may request a numeric adjustment. The request may be related to the CI or to one of the components that impact the CI, such as the intensity, color temperature, or color. For example, the request may request an additional 1000K of correlated color temperature (CCT) or 10% less intensity.

In addition, a circadian accent may be produced by a lighting fixture, such as a circadian effect light fixture. The circadian accent may be produced by directing light towards a user, such as by directing a high-intensity light towards the user. In addition, the circadian accent may be produced by directing light towards an effect area, such as an area on the wall having a bright color.

In some cases, a system may implement one or more of the innovations described herein. For example, a circadian effect light may produce a circadian accent based on information received from a distributed circadian model, or from a profile implementing a circadian strategy. In addition, a BCS may modify profiles implementing the circadian strategy based on information received from a distributed circadian model.

These illustrative examples are mentioned not to limit or define the disclosure, but to provide examples to aid understanding thereof. Additional examples are discussed in the Detailed Description, and further description is provided there.

BRIEF DESCRIPTION OF THE DRAWINGS

Features, examples, and advantages of the present disclosure are better understood when the following Detailed Description is read with reference to the accompanying drawings.

DETAILED DESCRIPTION

Figure 1:
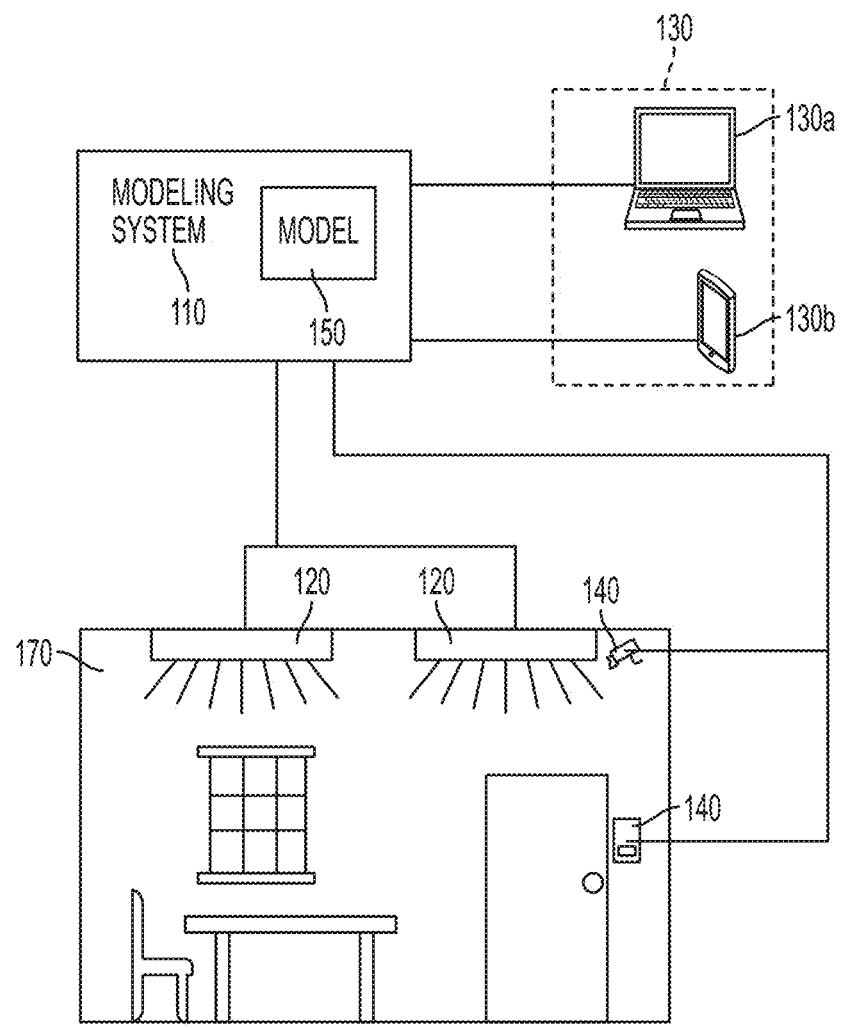
FIG. 1 depicts an exemplary system capable of providing or modifying a distributed circadian model, according to certain examples of the present disclosure.

Certain examples involve using a lighting system to determine and provide circadian factors in artificial light sources. The lighting system may include lighting fixtures (i.e., artificial light sources) that are controlled to generate a lighting profile within an area that tracks a circadian strategy for an occupant or a room. The circadian strategy may identify a desired level of circadian impact over a time period for the area. In an example, the desired level of circadian impact may promote wakefulness of occupants in a workplace or promote a regular sleeping schedule for an occupant of the area. The profile generated by the lighting fixtures tracks the circadian impact in a manner that implements the goals of the circadian strategy within the area illuminated by the lighting system.

The lighting profile generated by the lighting fixtures may rely on inputs received from external elements to track the circadian strategy. For example, a distributed circadian model may provide information to the lighting system describing circadian stimuli or circadian impact experienced within a modeled space (e.g., the area illuminated by the lighting fixtures). Using the distributed circadian model, the lighting system is able to adjust the profile based on circadian stimuli or circadian impact generated by sources other than the lighting fixture.

Further, the lighting profile may be generated by lighting fixtures that direct light toward circadian accents, or the lighting fixture may itself include lighting elements that generate circadian impact in the area. Moreover, the lighting system may track circadian impact resulting from natural sources or other lighting elements (e.g., computer monitors, luminous fixtures mounted on a wall, television screens mounted on a wall, or other light sources) that are not part of the lighting system. In tracking such circadian impact, the lighting system is able to control the lighting fixtures to generate the lighting profile that more accurately tracks the circadian strategy.

Distributed Circadian Model

A distributed circadian model may describe circadian stimuli or circadian impact (CI) levels experienced at a location. The distributed circadian model may describe the historic CI levels measured at the location, and/or the distributed circadian model may describe CI levels modeled at the location. The modeled location may be any space that receives natural or artificial light. The space that is modeled may be any area that receives light, such as a room in a building, an enclosure (e.g., an automobile), or an outdoor area. The distributed circadian model may include information about CI levels occurring within the modeled space. The CI levels may be related to ambient light in the modeled space, or to the output of light fixtures that produce light within the modeled space. In some cases, the circadian model may assign a dynamic value to the space, such as a value indicating a numeric or qualitative amount of circadian impact produced by the light within the modeled space.

The distributed circadian model may be updated based on additional information. For example, additional information may be received from sensors within the modeled space, from a lighting fixture having information about circadian factors of its produced light, from feedback provided by users of the space being modeled, from environmental sources (e.g., a weather report for the geographical region of the modeled space), or from any other suitable source of information. The distributed circadian model may be used to calculate personal exposure to circadian impact. For example, an application running on a mobile device may receive data from the distributed circadian model to estimate the amount of circadian impact experienced by a user of the mobile device. Additionally, the distributed circadian model may be used to calculate expected personal exposure to circadian impact throughout the remainder of the day. The expected personal exposure may be based on a typical schedule kept by an individual (e.g., time in an office, time commuting, etc.). Moreover, the expected personal exposure may be based on updates to a user's calendar that may change a user's personal exposure to circadian impact (e.g., additional meetings that expose a user to different levels of circadian impact).

The model may be updated based on information describing light output produced in the modeled space. A lighting fixture or network of lighting fixtures that provide light to a space may provide information to the distributed circadian model. The provided information may describe the light output that is produced by the lighting fixtures. For example, the provided information may describe CI levels associated with the light output. In addition, the provided information may describe attributes of the light output, and associated CI levels may be determined by an additional computing device.

In addition, the model may be updated based on data collected from sensors and sensor types, including fixed-location sensors and/or mobile sensors. Such data could include the intensity and/or the spectral content of incident light within the space. The data collected from these sensors may be used to determine CI levels in the modeled space. Fixed-location sensors may include occupancy sensors, cameras (e.g., security cameras), photocells, spectrometers, or other suitable sensors. Fixed-location sensors may measure the incident light at known locations within the modeled space (e.g., near a doorway, at a work surface). Mobile sensors may include wearable sensors (e.g., heart rate sensors, wearable exercise monitors, sleep monitors), or sensors that travel on or near the user (e.g., smart phone, tablet or laptop computer, automobile). Mobile sensors may gather information regarding the location of a user within the space, incident light levels at the user's location, and/or user feedback.

FIG. 1 depicts an exemplary system capable of providing or modifying a distributed circadian model. A modeling system 110 may receive information describing CI levels within a space 170. For example, the described space may be a room, such as an office within a building. The modeling system 110 may receive information from one or more lighting fixtures 120 and/or sensors 140 included within the space 170. In addition, the modeling system 110 may receive information from one or more user interfaces 130 (e.g., 130a and 130b). For example, user interface 130a may provide information describing space 170, such as dimensions, location of the lighting fixtures 120, a description of windows or skylights, a number of windows or skylights, window tinting, window size as a percentage of a wall area, orientation of windows, or any other suitable descriptive information. Based on the received information describing the space 170, modeling system 110 may generate a circadian model 150 describing the circadian impact received in the space 170.

The model 150 may indicate CI levels within the space 170. For example, model 150 may describe an intensity, a color, or a color temperature of incident light at one or more sub-locations within the space 170, such as at a work surface, near a window, at a particular area within the room (e.g., along a wall, within an office cubicle), or any other suitable sub-location. In some implementations, the model 150 may include one or more additional models, such as for one or more sub-locations within space 170. For example, if the space 170 is a large area or includes sub-locations with widely varying levels of incident light (e.g., a sports arena), model 150 may include an additional model describing a particular sub-location (e.g., a sports field, a seating section, an interior corridor). In some implementations, the model 150 may include a value indicating a CI level of space 170 (or a sub-location). The value may be represented as a unit of exposure to circadian impact (e.g., circadian stimulus unit, equivalent melanopic lux), as a percentage, as a qualitative value (e.g., "low" or "high" CI levels), or as any other suitable representation.

The model 150 may be modified based on additional information describing the space 170. For example, modeling system 110 may receive additional information from one or more of the light fixtures 120, user interfaces 130, or sensors 140. The additional information may indicate a change in light output, a change in dimensions of the space 170 (e.g., remodeling), a change in a location of a work surface, or any other suitable information. In some implementations, model 150 may be modified to include an additional model based on additional information indicating a potential sub-location. For example, a user interface 130b may indicate that a corner area of space 170 is partitioned, and receives relatively low level of light from fixtures 120. In addition, sensor 140 (e.g., a security camera, an occupancy sensor) may indicate a low level of light in the corner area. Responsive to receiving such indications, modeling system 110 may indicate the corner area of space 170 as a sub-location. In addition, modeling system 110 may modify the model 150 to include an additional model describing the corner area.

In some implementations, model 150 may be modified based on additional information received from one or more environmental sources (e.g., sources not included within space 170). For example, in response to receiving a weather report for the geographical region around space 170, modeling system 110 may modify the model 150 based on an amount of sunlight indicated by the weather report. In addition, model 150 may be modified based on data derived from received information. For example, responsive to receiving information indicating a sunrise/sunset time, modeling system 110 may derive data indicating an expected amount of sunlight at a particular time of day, and model 150 may be modified based on the derived data. In an example, the model 150 may be implemented within a controller of the lighting fixtures 120, or the model 150 may be implemented at a centralized server of a lighting system (e.g., such as a centralized lighting control system of a building).

Background Circadian System

A background circadian system ("BCS") may implement a circadian strategy for one or more lighting fixtures. The strategy may be selected to promote an outcome, such as a psychological (e.g., short-term or alerting) outcome or a circadian (e.g., long-term) outcome. For example, a company may include a BCS in a factory to promote a short-term psychological outcome of wakefulness (e.g., for each shift of workers). Alternatively, a person may include a BCS in a residence, to implement a circadian strategy that promotes a long-term circadian outcome of a regular sleeping schedule. Strategies may be intended to provide exposure to levels of circadian impact ("CI"), such as light having a particular intensity, color, or color temperature. The strategy may be associated with one or more strategic profiles. A profile (e.g., a circadian impact profile) may include a series of CI levels output by a lighting fixture, such as to achieve a particular circadian strategy. In an example, a profile may use the distributed circadian model described above with respect to FIG. 1 as a factor to control the lighting fixture output to generate the CI levels that achieve the circadian strategy.

Figure 2:
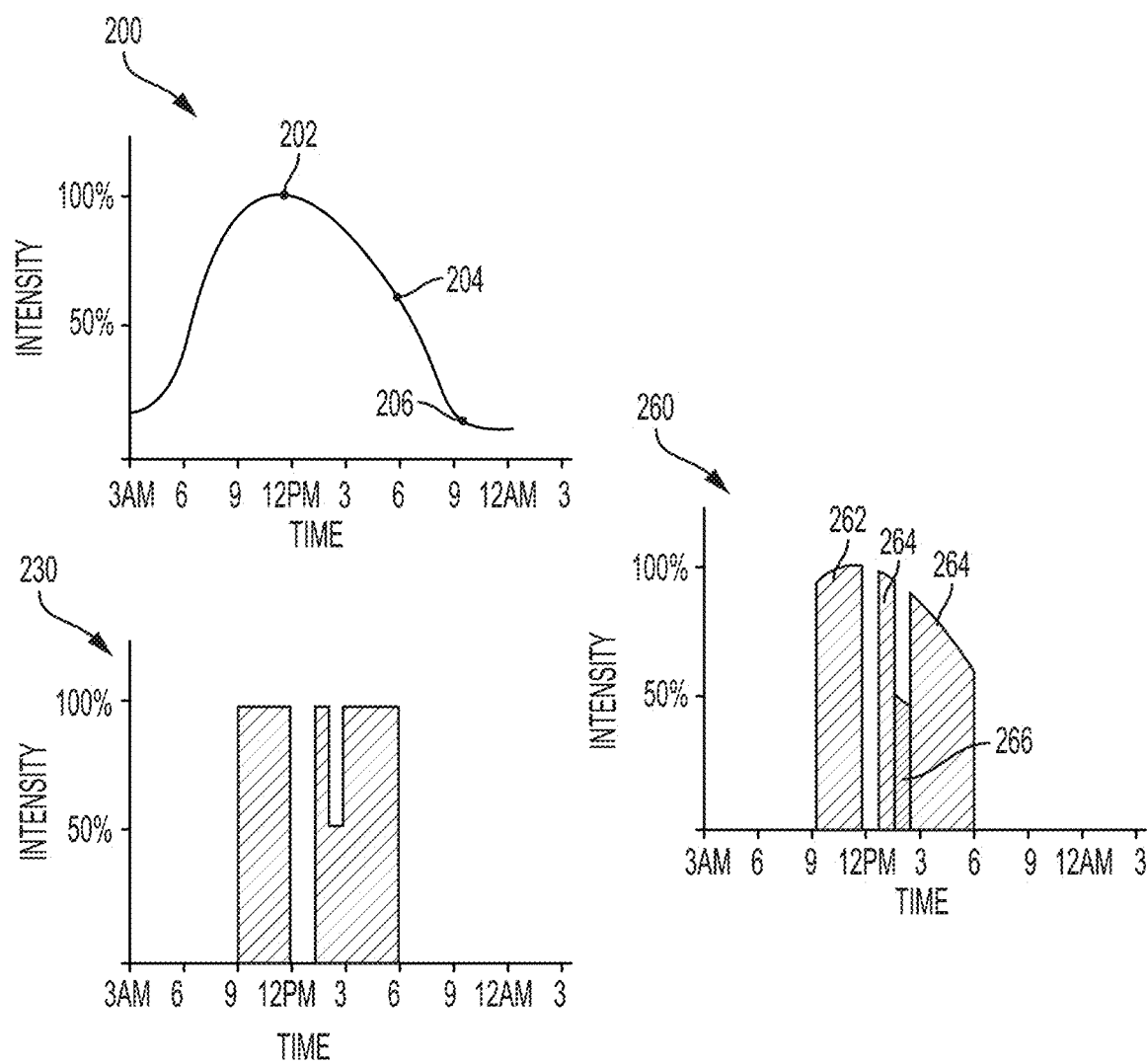
FIG. 2 depicts an exemplary profile, an exemplary requested output, and an exemplary combined output of circadian impact, according to certain examples of the present disclosure.

Referring now to the drawings, FIG. 2 includes a depiction of an exemplary profile 200, an exemplary requested output 230, and an exemplary combined output 260. Profile 200 may include a series of light intensity levels over a 24-hour period, and may be associated with a circadian strategy to promote a regular sleeping schedule. For example, the strategy may include exposure to higher intensity light in the morning hours, medium intensity light in the afternoon, and lower intensity light in the evening. In addition, the strategy may include exposure to higher-intensity blue spectrum in the morning, and lower-intensity blue spectrum in the afternoon and evening. Other exemplary strategies (including strategies that do not span 24 hours) will be apparent to those skilled in the art.

Profile 200 may include information describing an intensity associated with a time (e.g., a time of day, a time point in the profile). For example, profile 200 may indicate an increasing intensity during morning hours, up to an intensity of about 100% at a time of about noon, such as at point 202. The profile 200 may indicate a gradually decreasing intensity during the afternoon, to an intensity of about 60% at about 6:00 PM, such as at point 204. The profile 200 may indicate a more rapidly decreasing intensity during the evening until a few hours before a targeted bedtime, such as a decrease in intensity to about 20% at about 9:00 PM, such as at point 206. In addition, the profile 200 may indicate other CI components. For example, the profile 200 may indicate an increasing amount of blue light during morning hours, up to a time of about noon, a decreasing amount of blue light during afternoon and evening hours, up to a time of about 8:00 PM, and a minimal amount of blue light during night hours, up to a time of about 4:00 AM. The profile 200 may also indicate a correlated color temperature throughout the day.

Requested output 230 may include various levels of light output, based on inputs received by a lighting fixture. For example, a person working in an office may turn the lights on when they arrive around 9:00 AM, and may turn the lights off when they leave at 6:00 PM. In addition, the person may turn the lights off between noon and 1:00 PM for lunchtime, and may dim the lights between 2:00 PM and 3:00 PM for a presentation. The inputs provided by the person (e.g., turning the lights on or off, dimming) may indicate the requested output 230, which in this example relates to intensity. The requested output may also be provided by a sensor. For example, an occupancy sensor may determine that the office is unoccupied between noon and 1:00 PM and may communicate the occupancy information as the requested output.

A combined light output, such as depicted by combined output 260, may be produced based on a combination of the profile 200 and the inputs provided with regards to requested output 230. For example, a lighting fixture may receive information describing a profile, such as from a BCS, and an input indicating a requested output, such as from a light switch used by a person. The BCS may provide a modifying factor that describes a CI level based on both the profile and any requested output. The modifying factor may be associated with a time. The modifying factor may be a numeric CI level at a particular time. The modifying factor may also be an offset CI level or an offset percentage. Alternatively, the modifying factor may be a combination of an intensity value, a CCT value, and a color value at a particular time. In some instances the profile may relate only to intensity or CCT. In these instances, the modifying factor may be a percentage or numeric value representing the intensity level or CCT at a particular time.

The lighting fixture may produce output based on the combination of the received modifying factor and input. For example, combined output 260 may include a region 262, between about 9:00 AM and noon, based on the received input to turn the lights on (related to requested output 230) and an intensity of near 100% (related to the profile 200). Combined output 260 may include minimal or no light output between noon and 1:00 PM, based on the input to turn the lights off. The combined output 260 may resume the profile 200 at 1:00 PM, based on the input to turn the lights on and the modifying factor (including the time associated with the modifying factor). When the profile 200 is resumed based on the input to turn the lights on, the resumption of the profile 200 takes into account the passage of time while the lights were off. For example, when the light is turned on at 1:00 PM, the combined output 260 resumes tracking the profile 200 at the 1:00 PM intensity value of the profile 200.

Region 264 may be based on the received input to turn the lights on (related to requested output 230) and a gradually decreasing intensity from about 100% to about 60% (related to the profile 200). Region 266 may be based on the received input to dim the lights (related to requested output 230) and a gradually decreasing intensity from about 100% to about 60% (related to the profile 200). In addition, the region 262 may include an increasing amount of blue light, and regions 264 and 266 may include a decreasing amount of blue light (related to the profile 200).

Implementations of profiles may be cyclical (e.g., a completed occurrence of profile 200 may be followed by a repetition of profile 200), or a completed profile may be followed by a different profile, or by a default state.

The profile may be adjusted based on the season, the time of sunset or sunrise, or other factors. If sunset is later in the evening (e.g. closer to bed time) then the profile may change to increase the amount of CI in the first part of the day (e.g. the morning).

The profile may be created using a "wizard" type user interface. The user may be asked a series of questions to elicit information needed to create a profile. The types of questions may be different for different types of uses. For example, the questions posed to create a profile for a commercial or industrial space (e.g., a profile that tracks a circadian strategy) may differ from the questions posed to create an individualized user profile. Exemplary questions may include one or more of the following: "what are the office hours", "when do you go to sleep at night", "are there windows in the office", "what is the latitude/longitude", etc. Based on the answers to these questions, the profile may be automatically generated using an algorithm.

Figure 3:
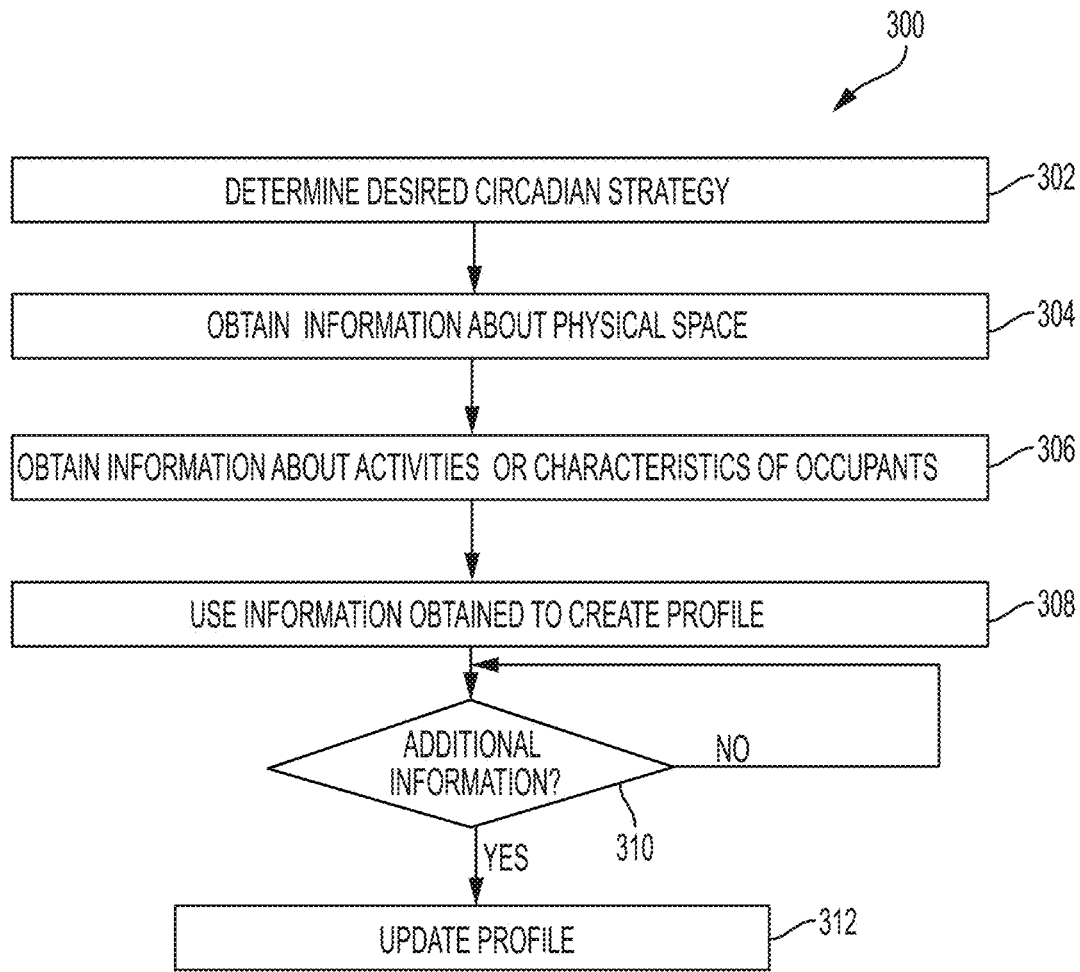
FIG. 3 depicts a method for generating a profile, according to certain examples of the present disclosure.

FIG. 3 illustrates one method 300 for generating a profile. The method 300 may begin at block 302 by presenting the user with a series of questions or prompts to determine the desired circadian strategy, such as promoting a regular sleep schedule, promoting wakefulness during a certain period of the day, overcoming jetlag, or helping adjust to time changes. The method 300 may also present the user with a series of questions related to the physical space at block 304. These questions may request information about the location of the space (e.g., latitude/longitude) or characteristics of the space (e.g., windows and window orientations). Additional questions may also be presented at block 306 to determine information about the activities of the occupant(s) of the space (e.g., desired bedtime, type of occupant activity) or characteristics of the occupant(s) relevant to circadian impact (e.g., age). Other questions directed to other types of information may also be presented.

Once the information is obtained, the information is used at block 308 to create a profile to achieve the desired strategy. The profile may be represented as a series of CI values over time. This is type of profile is an absolute profile. For example, the profile may specify a first numeric CI value from time t1 to time t2 and then a second numeric CI value from time t3 to time t4. Alternatively, the profile may be represented as a series of offset values over time. This type of profile is a relative profile. For example, the profile may specify a first numeric or percentage offset from time t1 to time t2 and then a second numeric or percentage offset from time t3 to time t4. Once the profile is created, it may be modified. The modifications may be based on additional information received at block 310 from the user or the occupant(s) or additional information received at block 310 from or about the space (e.g., information from sensors, information about sunrise/sunset times). At block 312, the profile may be updated based on the additional information.

Figure 4:
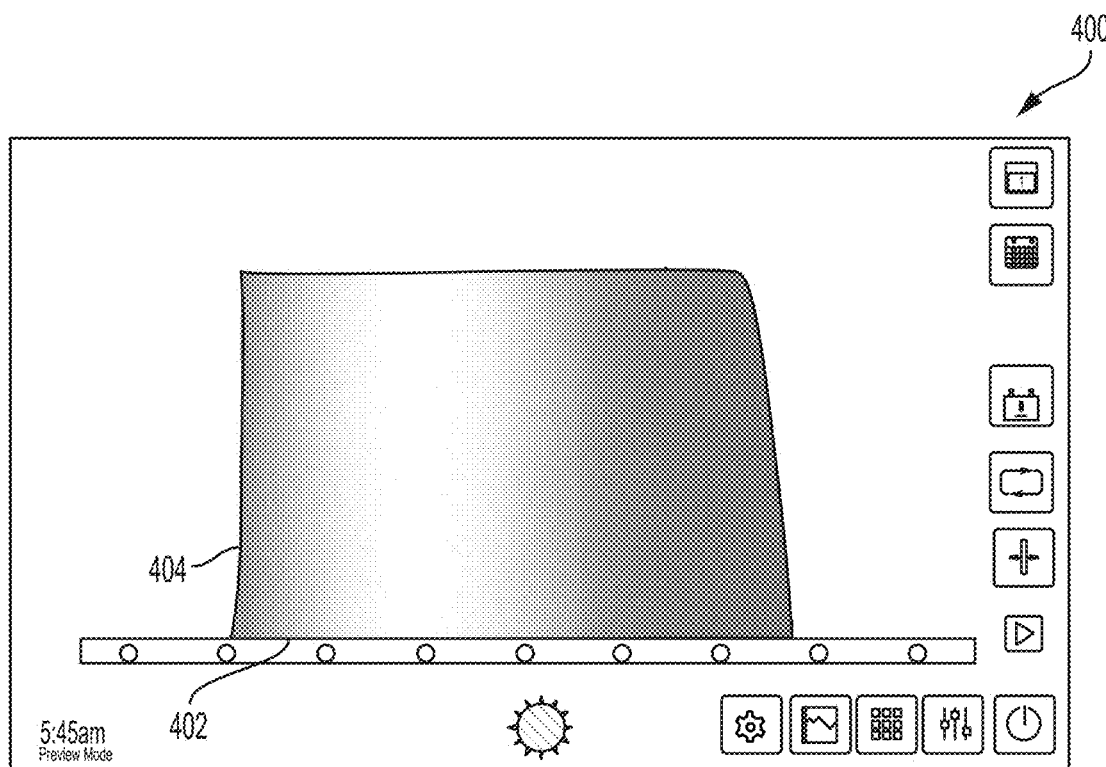
FIG. 4 depicts a profile that changes correlated color temperature over time, according to certain examples of the present disclosure.
Figure 5:
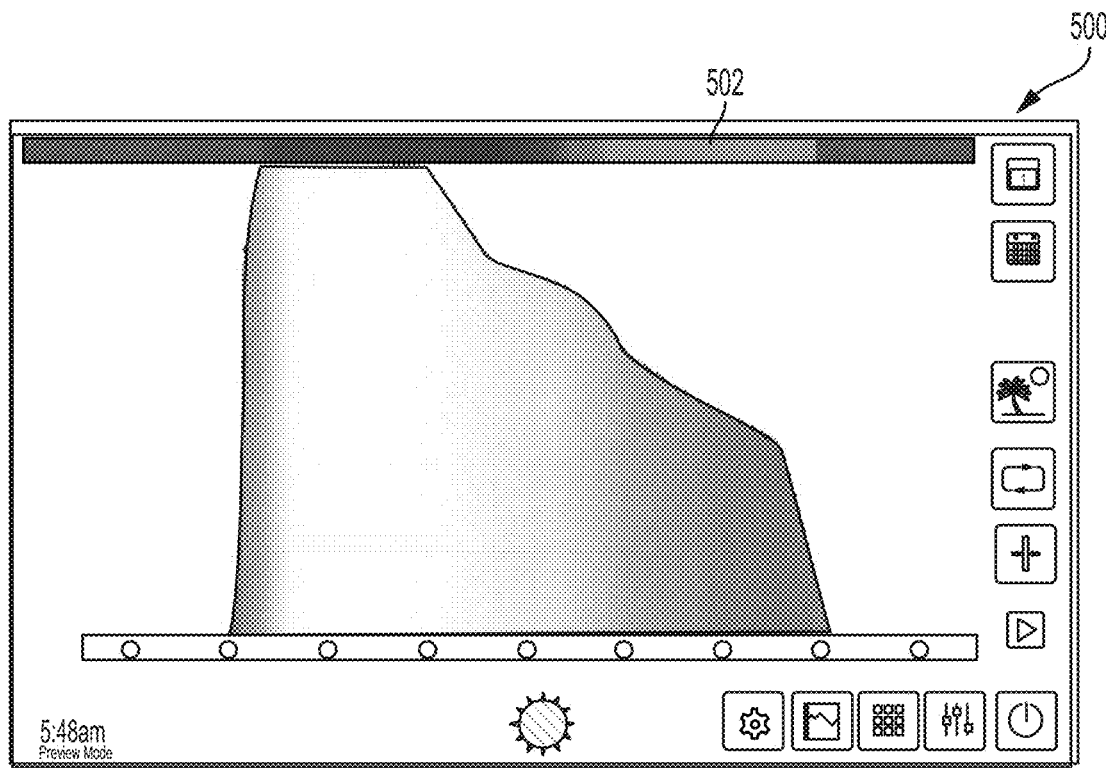
FIG. 5 depicts a profile appropriate for an office in the summer, according to certain examples of the present disclosure.
Figure 6:
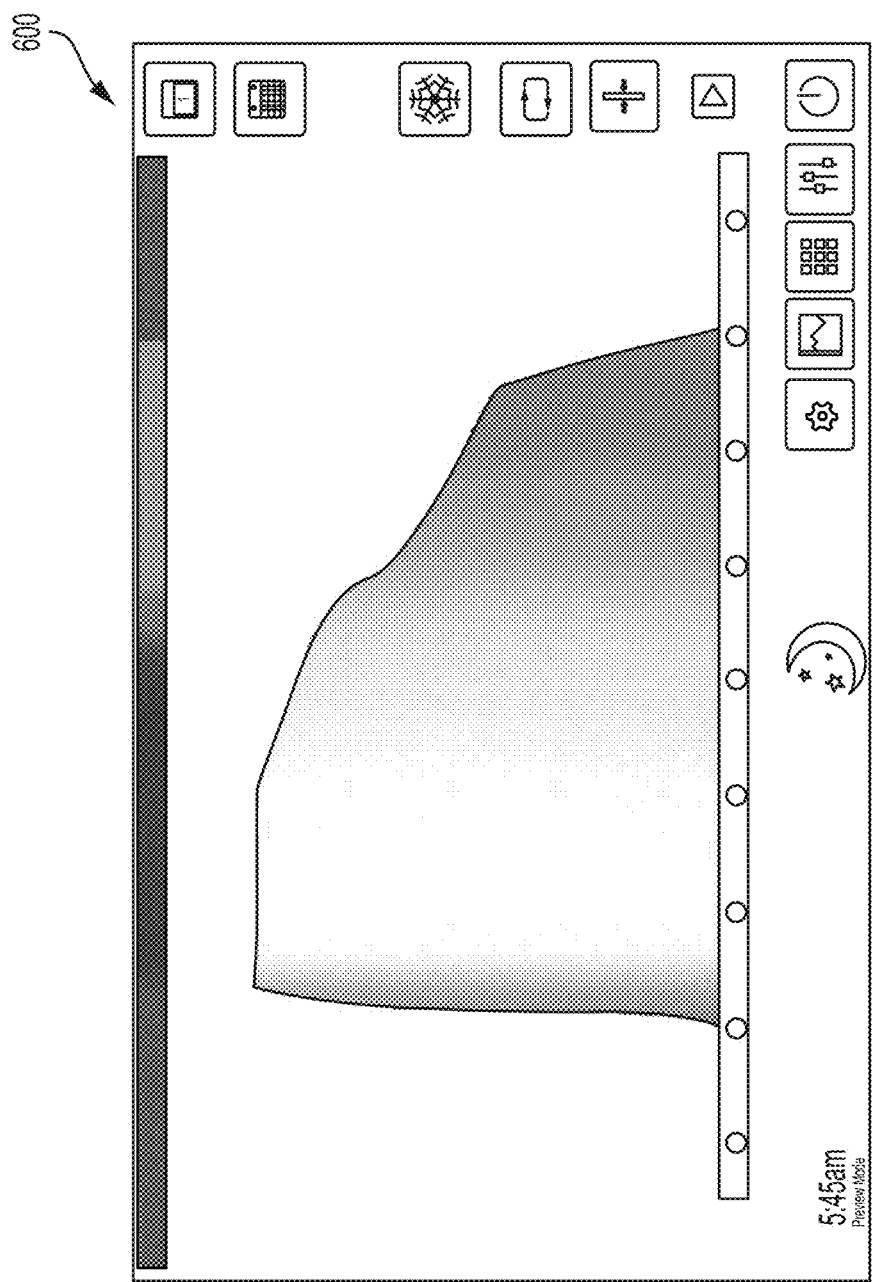
FIG. 6 depicts a profile appropriate for the same office as FIG. 5 in the winter, according to certain examples of the present disclosure.

FIGS. 4-6 illustrate the display of exemplary profiles, which may be provided to a user once the profile is created. FIG. 4 illustrates a profile 400 that changes CCT over time. An x-axis 402 relates to time and a y-axis 404 relates to intensity. The intensity is represented by the height of the curve and the CCT is represented by color under the curve. To transition from changes to a numeric CI level to changes in lighting output parameters, a CI model of the space may be used. For example, the model may include a spectrum (e.g., how much of each wavelength is output), an intensity, and a distribution of a light source. Further, the model may include information relating to walls, a ceiling, a floor, furniture and finishes of such components located in the space. Based on the CI model, a controller may track changes to the numeric CI level by changing an intensity, CCT, color value, or any combination thereof of a lighting fixture. The translation from a numerical CI level to changes of an output of the lighting fixture may take place in a background server, such as a background circadian system 1010 discussed below with respect to FIG. 10, or the translation may take place in a controller of the lighting fixture. As illustrated, the CCT changes over time, but the intensity remains constant throughout most of the day. FIG. 5 illustrates a profile 500 that may be appropriate for an office in the summer. The profile changes intensity, CCT and color over time. Intensity and CCT are represented in the same manner as in FIG. 4. The color is represented by different colors in the horizontal bar 502 above the intensity curve. FIG. 6 represents another profile 600 that may be appropriate for the same office as FIG. 5, but in the winter.

Comparing the profiles in FIGS. 5 and 6 illustrates how the intensity and CCT may be changed to adjust for seasonal variations. Further, the profiles 400, 500, and 600 may change based on seasonal patterns and global positioning of a location of interest where the profiles 400, 500, and 600 are implemented. For example, different global positions (e.g., longitudes and latitudes, orientations, local weather patterns) of the location of interest may experience different levels of natural light throughout the day at similar times. A location in Fargo, North Dakota experiences more light later into the evening in summer than Mexico City on the same day based on differences in latitude. Accordingly, the profile of a room in Fargo will be different than the profile of a room in Mexico City. Further, an astronomical clock may change the profiles 400, 500, and 600 based on where a location of interest is located within a time zone. For example, a city located in a far western portion of a time zone will have sunset occur later in the day than a city located in a far eastern portion of the time zone.

Figure 7:
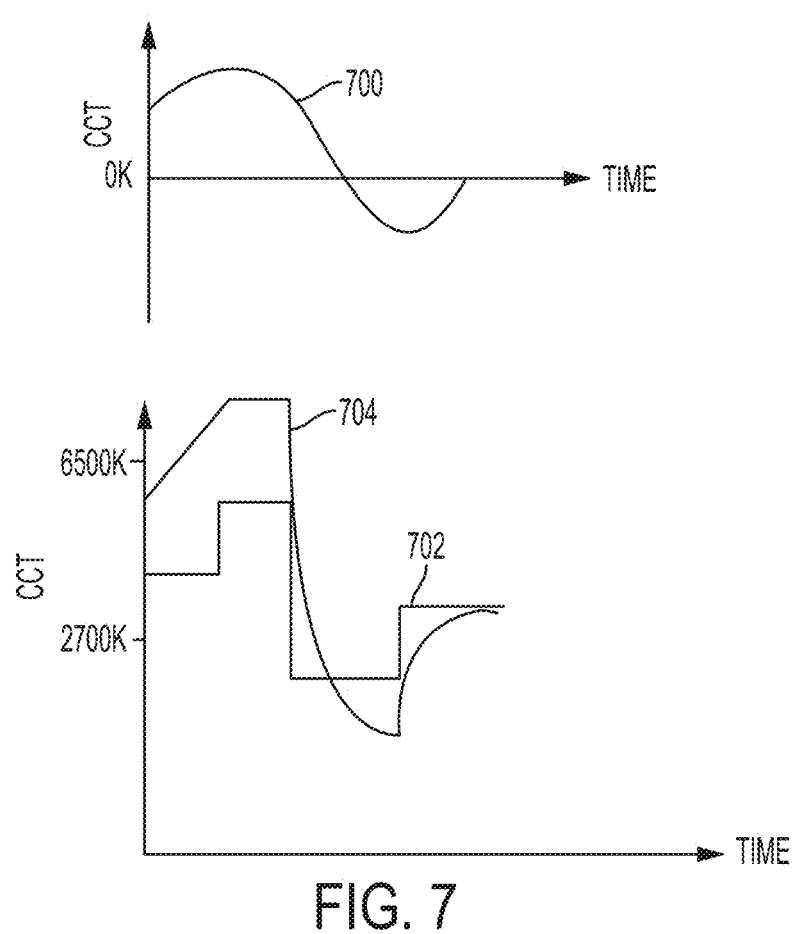
FIGS. 7-9 depict examples of combined light outputs, according to certain examples of the present disclosure.

FIG. 7 illustrates another example of a combined output. The profile 700 is a relative profile and specifies a CCT offset over time. In this example, the requested output 702 relates to CCT. The user may select a preset scene from a control panel to provide the requested output. The combined output 704 reflects the CCT offset values added to the requested output 702.

Figure 8:
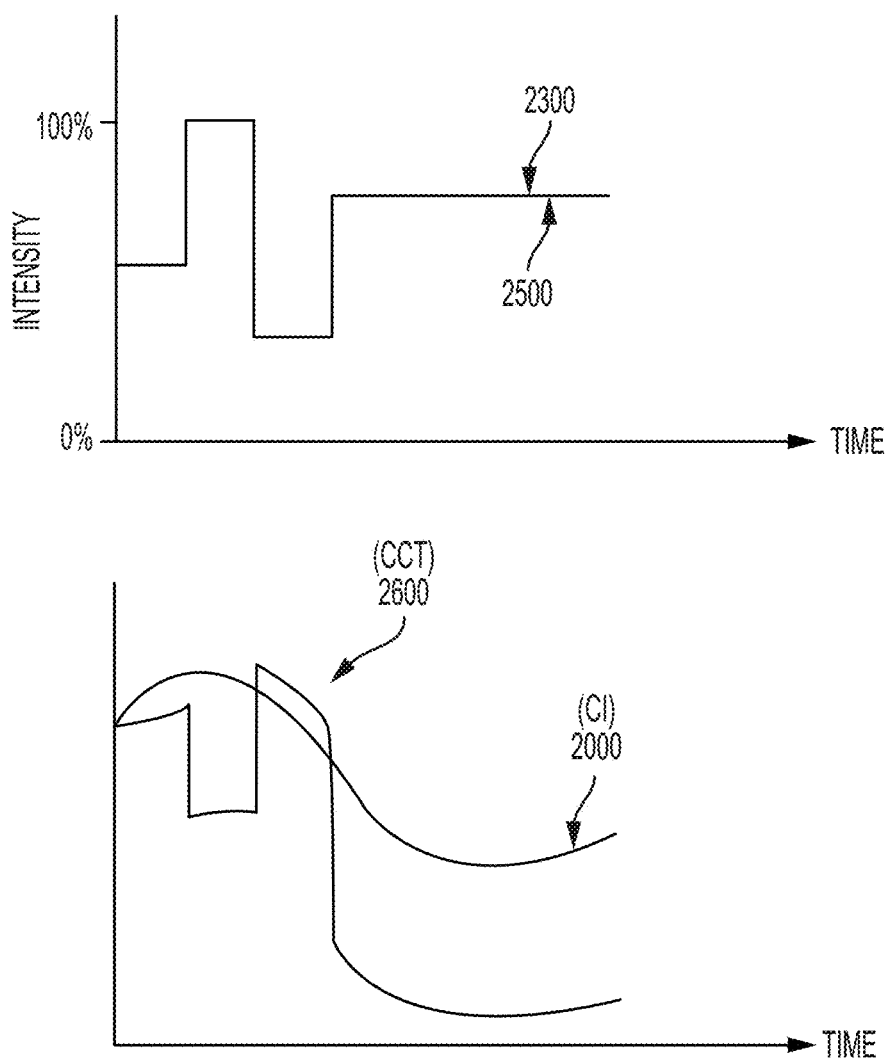

FIG. 8 illustrates another example of a combined output. The profile 2000 is an absolute profile and specifies CI values over time. In this example, the requested output 2300 relates to intensity. The intensity 2500 of the combined output tracks the requested intensity output 2300. The CCT of the combined output 2600 may be adjusted in certain regions to compensate for the requested intensity output in those regions so that the CI of the combined output better tracks the profile. For example, when a high CI value is indicated in the profile and the requested intensity output is not high enough to produce the high CI value, the CCT may be increased. Other adjustments may also be made in those regions including, but not limited to adjusting a color accent.

Figure 9:
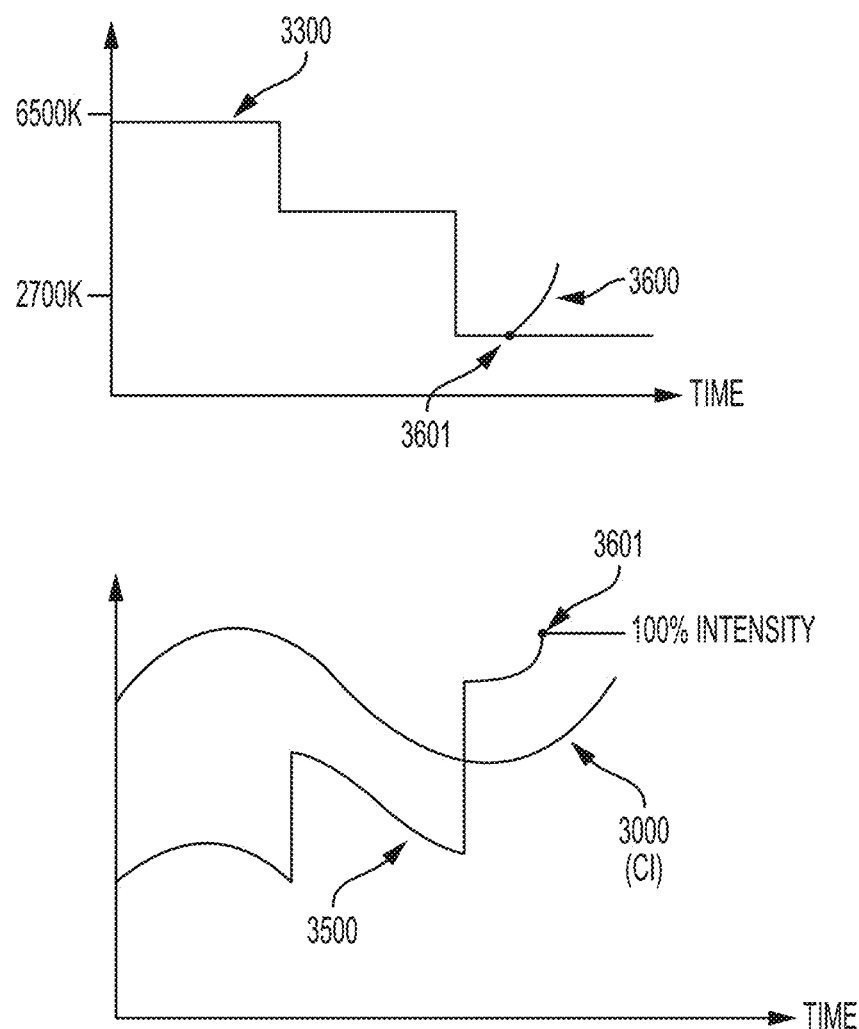

FIG. 9 illustrates another example of a combined output. The profile 3000 is an absolute profile and specifies CI values over time. In this example, the requested output 3300 relates to CCT. The CCT 3600 of the combined output tracks the requested CCT output 3300 until point 3601. The intensity 3500 of the combined output may be adjusted in certain regions to compensate for the requested CCT in those regions so that the CI of the combined output better tracks the profile. However, at point 3601, the intensity can no longer be adjusted since it is at 100%. Since the CI target is not met, the CCT 3600 of the combined output is adjusted and the CCT of the combined output diverges from the requested CCT after point 3601. The adjustment of the CCT 3600 beginning at point 3601 allows the combined output to better track the profile. Other adjustments may also be made in selected regions including, but not limited to adjusting a color accent.

The requested output is not limited to adjusting only intensity or CCT, but may include adjustments to both the intensity and the CCT. If the requested output relates to both CCT and intensity, then adjustments to both the CCT and the intensity of the combined output may be made, as well as adjustments to a color accent. The adjustments may be made according to a priority. For example, adjustments to the intensity of the combined output may be made first, adjustments to CCT of the combined output may be made next, and adjustments to the color accent, may be made after the CCT adjustments. Other priorities may be used, including priorities that consider other aspects or components. In an example, the requested output may be controlled by adjusting a group of parameters associated with a lighting fixture including the intensity of the lighting fixture, the CCT of the lighting fixture, a spectrum of the lighting fixture (e.g., how much of each wavelength is in the requested output), a spatial distribution of the lighting fixture (e.g., where and how the requested output is concentrated), or any combination thereof.

A BCS may be in communication with a lighting network. The lighting network may include one or more lighting fixtures and/or control modules. The lighting fixtures may be capable of adjusting their output based on received information. In addition, the control modules may be capable of generating instructions (e.g., for the lighting fixtures) based on received information. The BCS may provide information, such as a modifying factor, to one or more of the components on the lighting network, based on a circadian strategy implemented by the BCS. The components (e.g., lighting fixtures or control modules) may produce output based in part on the information provided by the BCS. For example, the lighting network may modify the light output of the fixtures based in part on a modifying factor received from the BCS.

Figure 10:
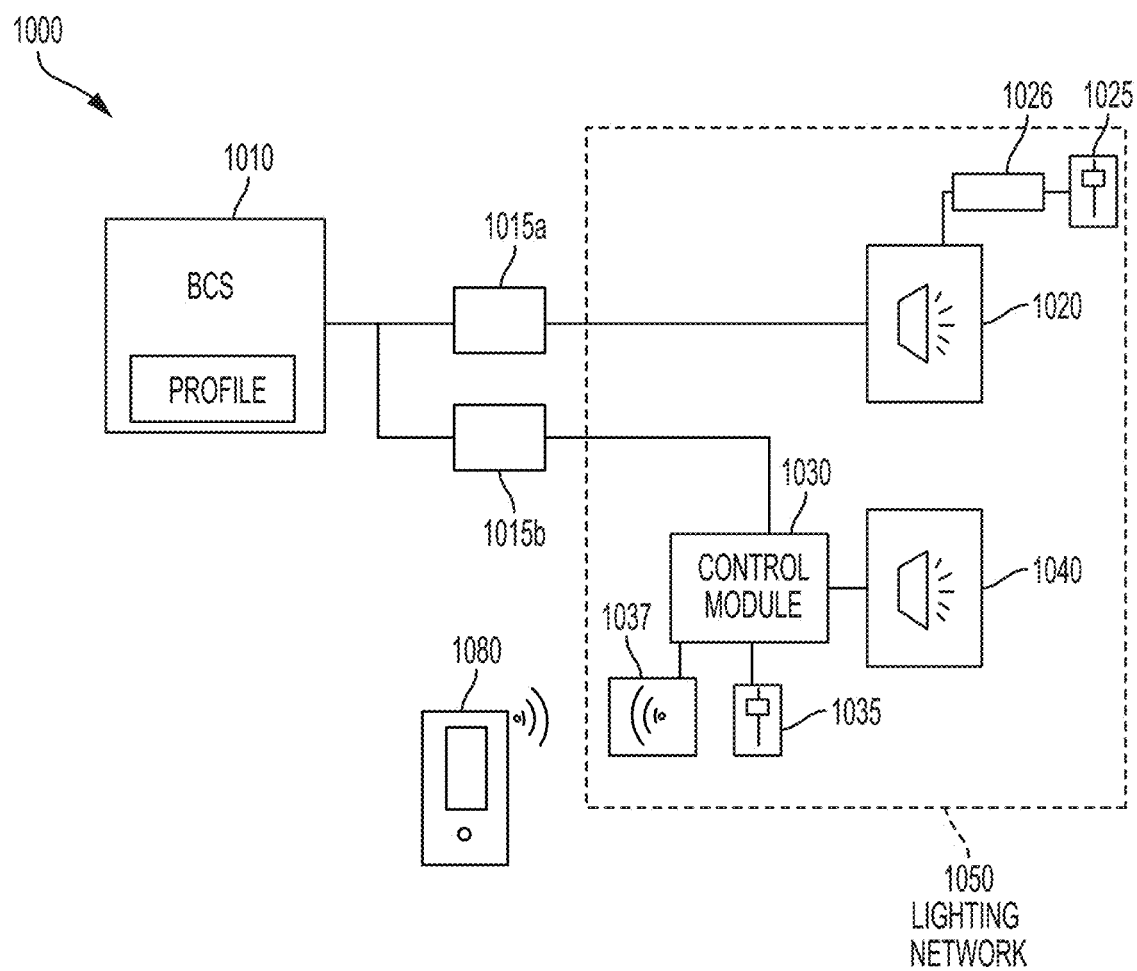
FIG. 10 depicts an exemplary system capable of producing light output based on a circadian strategy, according to certain examples of the present disclosure.

FIG. 10 depicts an exemplary system 1000 capable of producing light output based on a circadian strategy. A BCS 1010 may communicate with one or more components of a lighting network 1050. Communication may be via wired and/or wireless communication techniques, such as network wiring, a Wi-Fi modem, data carried on the Internet or a private network, or any other suitable communication technique. The lighting network 1050 may include lighting fixtures 1020 and 1040, a control module 1030, and one or more input devices, such as switches 1025 and 1035. An antenna 1037 may be included in control module 1030 (or in any other component of the lighting network 1050). Additional input may be received via antenna 1037, such as from a personal computing device 1080, or other suitable devices.

The additional input may include user requests to adjust the CI based on personal data from the user so that the user may achieve a desired CI. The data may include the user's CI levels from earlier time periods, demographic information about the user, such as age or gender, physical or physiological information, or other types of data.

The BCS 1010 may include a profile 1013 that is associated with a circadian strategy. The profile 1013 may include a series of CI levels intended to promote an outcome (e.g., promoting a regular sleeping schedule). The profile 1013 may be associated with a time of day, such that a particular CI level is associated with a particular time or time range. A modifying factor, such as modifying factors 1015a and 1015b (collectively, 1015) may be based on the profile 1013 and a current time received (or determined) by BCS 1010. The BCS 1010 may provide modifying factor 1015 to the lighting network 1050. For example, lighting fixture 1020 may receive modifying factor 1015a, and control module 1030 may receive modifying factor 1015b. In one implementation, the BCS 1010 streams the modifying factors to the lighting network 1050.

In response to receiving modifying factor 1015, components of lighting network 1050 may produce output based in part on the modifying factor 1015. For example, lighting fixture 1020 may modify its light output based on the modifying factor 1015a, such as by transitioning from a powered-off state to a powered-on state (or the reverse transition). In addition, lighting fixture 1020 may modify one or more attributes (e.g., intensity, color) of its light output. For example, if the modifying factor 1015a indicates a CI level associated with a time range of mid-morning, lighting fixture 1020 may increase the intensity of its light output, or produce light output having a relatively high amount of blue light.

In addition, control module 1030 may modify its output based on the modifying factor 1015b, such as by providing instructions to the lighting fixture 1040. The provided instructions may indicate a modification of the output of lighting fixture 1040, such as a transition between powered-on and powered-off states, or a modification of an attribute of light output produced by lighting fixture 1040.

In some implementations, the output of lighting network 1050 may be based on a combination of the modifying factor 1015 and other information. The combination may be determined by one or more components that are capable of performing operations to adjust light output. For example, lighting fixture 1020 may be capable of performing operations to adjust its own light output. In addition, control module 1030 may be capable of performing operations to generate instructions that are provided to lighting fixture 1040, and lighting fixture 1040 may adjust its light output responsive to receiving the instructions.

Lighting fixture 1020 may receive input 1026 from an input device, such as switch 1025. The input 1026 may indicate a requested light output of lighting fixture 1020, such as increasing the light output intensity, selecting a lighting scene (e.g., dimming lights for a presentation), or turning off the fixture 1020. Responsive to receiving the modifying factor 1015a and the input 1026, lighting fixture 1020 may produce output based on a combination of modifying factor 1015a and input 1026. For example, if the modifying factor 1015a indicates a CI level associated with a time range of mid-morning and the input 1026 indicates a lighting scene with dimmed lights, the lighting fixture 1020 may produce light output having a reduced intensity and a relatively high amount of blue light (e.g., dimmed bluish-white light).

The control module 1030 may be used to implement the CI illustrated by FIGS. 8 and 9. For example, the modifying factor 1015b may reflect values related to the profile and the requested output (e.g., CCT or intensity) may be received by the control module via a switch 1035 or transmitted to the control module via antenna 1037. The control module may control the output of lighting fixture 1040 to produce the combined output shown in FIGS. 8 and 9. Alternatively, the requested output may be provided to the BCS and the BCS may generate an adjusted modifying factor for lighting fixture 1040.

Figure 11:
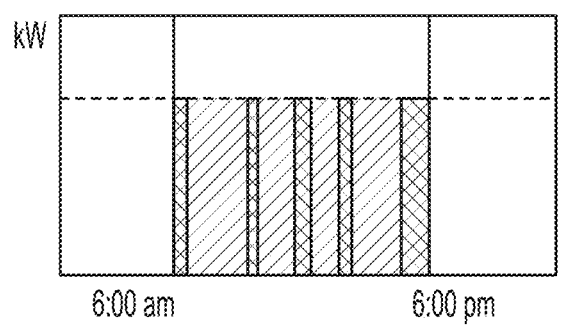
FIG. 11 depicts an exemplary requested output from an occupancy sensor placed in an office, according to certain examples of the present disclosure.
Figure 12:
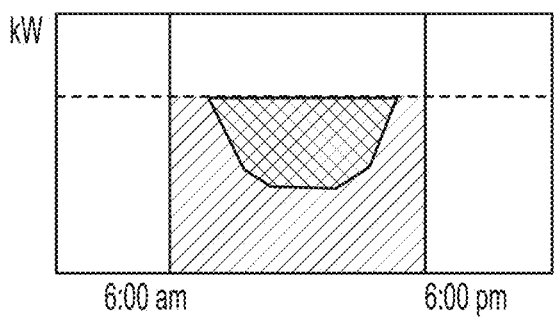
FIG. 12 depicts an exemplary requested output from a daylight harvesting sensor placed in a space that receives daylight, according to certain examples of the present disclosure.

The requested output may also be provided by a sensor, such as an occupancy sensor or a daylight harvesting sensor. FIG. 11 illustrates an exemplary requested output from an occupancy sensor placed in an office and FIG. 12 illustrates an exemplary requested output from a daylight harvesting sensor placed in a space that receives daylight.

In an example, the modifying factor may be overridden. For example, lighting of a patient room in a hospital may have an override instruction or an override state, such as an emergency switch, to provide light output that is not modified by a profile or switch during emergency situations. Upon completion of the event that prompted the override function, the lighting may return to an output designated by the modifying factor. In an example, the lighting may return to the output designated by the modifying factor based on passage of a predetermined amount of time. For example, the override function may include a default timer that overrides the output designated by the modifying factor for 5 minutes. Upon completion of the 5 minute timer, the lighting may return to the output designating by the modifying factor. In another example, the lighting may return to the output designated by the modifying factor based on an automated trigger (e.g., no longer detecting occupant movement in the room).

Figure 13:
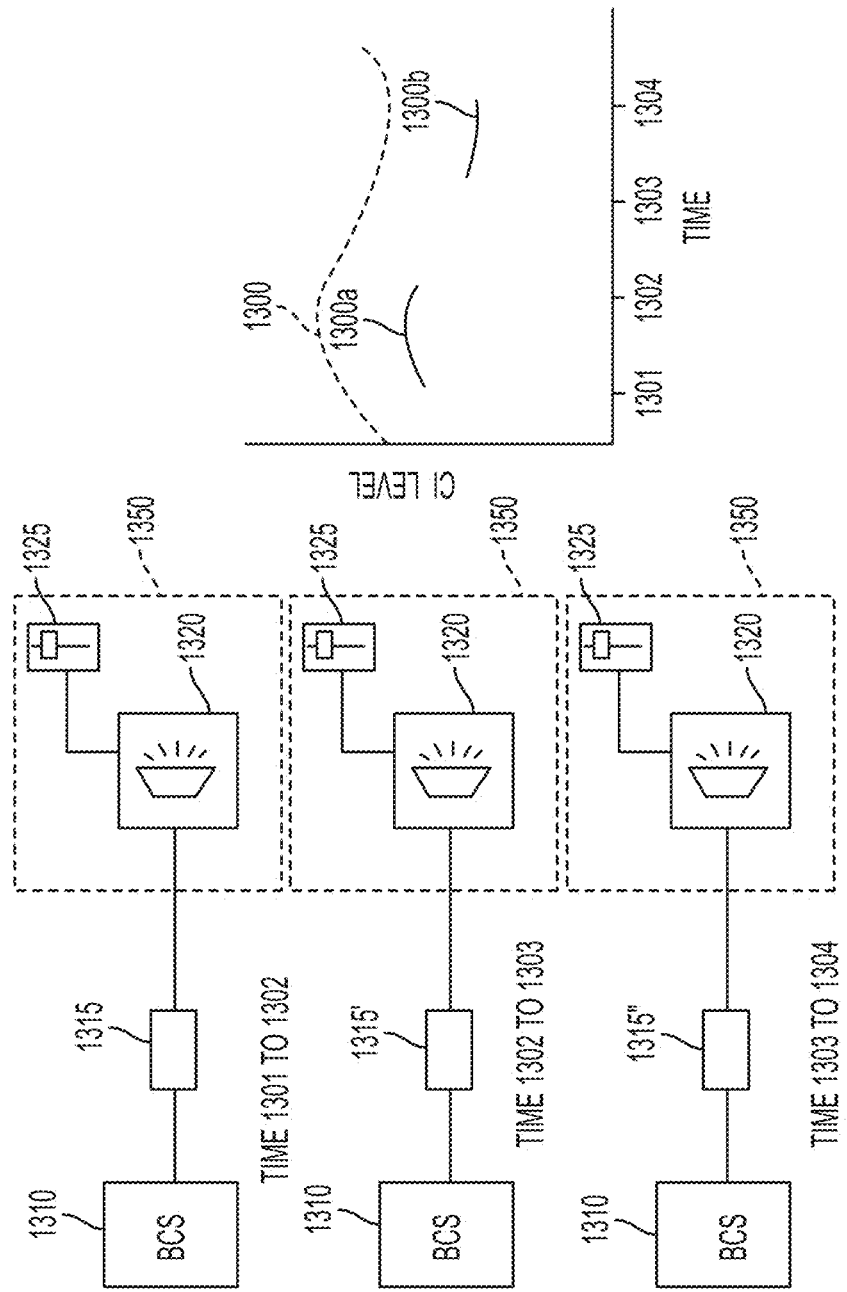
FIG. 13 depicts an exemplary system that is capable of resuming light output according to a strategic profile, according to certain examples of the present disclosure.

In some implementations, a lighting network may resume a level of light output indicated by a profile based in part on information provided by a BCS. For example, a lighting network may resume producing light output according to a profile, based on a modifying factor associated with the profile. FIG. 13 depicts an exemplary system that is capable of resuming light output according to a strategic profile. A BCS 1310 may implement a profile 1300 (indicated as a dotted line) that is associated with a circadian strategy, such as to promote wakefulness during an employee shift. Profile 1300 may have a 8-hour time span, and may repeat upon completion of the time span. A modifying factor 1315, 1315', or 1315" may describe the profile 1300, such as describing a CI level (or a range of CI levels) associated with a specific time or time range during the time span. In an example, the CI level may be measured with a spectrometer or a photometer with an appropriate filter. The spectrometer or photometer readings may be fed into a calculator to determine a numeric value of the CI level.

The BCS 1310 may communicate with a lighting network 1350. The lighting network 1350 may include a lighting fixture 1320 and an input device 1325. The lighting fixture 1320 may by capable of adjusting its output based on received information. In some cases, the lighting network 1350 may also include additional input devices or lighting fixtures, including lighting fixtures that produce output based on instructions received from control modules.

During a first range of times, the lighting network 1350 may produce light output according to profile 1300. The light output may be based on a modifying factor 1315 received from BCS 1310 and input received from input device 1325. The input device 1325 may specify a relative adjustment of the profile 1300. For example, during the time range indicated between points 1301 and 1302, the input from input device 1325 may indicate a requested output of about 90%, or slightly less than maximum. The input may be determined by the relative position of the slider. In addition, the modifying factor 1315 may describe CI levels between points 1301 and 1302 on the profile 1300. Based on a combination of this information, lighting fixture 1320 may produce light output having a range of CI levels 1300a.

During a second range of times, lighting network 1350 may modify its light output based on the input from device 1325. In this case, the input from device 1325 between points 1302 and 1303 indicates a powered-off state (e.g., a requested output of about 0%). Based on this information, lighting fixture 1320 may modify its output such that the input from device 1325 overrides the modifying factor 1315' associated with the profile.

In some cases, the lighting network may receive additional information indicating a low-power state (e.g., standby or "energy saver" mode), or a high-intensity state (e.g., emergency mode). Alternatively, the additional information may indicate that the lighting network modify its light output based on a second strategic profile instead of (or in combination with) profile 1300.

During a third range of times, lighting network 1350 may modify its light output again to resume output according to profile 1300. For example, during the time range indicated between points 1303 and 1304, the input from input device 1325 may indicate a requested output of about 90% or slightly less than maximum. In addition, the modifying factor 1315 may describe CI levels between points 1303 and 1304 on the profile. Based on a combination of this information, lighting fixture 1320 may produce light output having a range of CI levels 1300b. The resumed output from lighting fixture 1320 may include CI levels that are based on the time associated with points 1303 to 1304. For example, if point 1302 represents 12:00 PM and point 1303 represents 1:00 PM, the resumed output from the lighting fixture 1320 may include CI levels that track the profile 1300 at 1:00 PM instead of at 12:00 PM when the lighting fixture 1320 entered the powered-off state. Thus, the CI levels 1300b take into account the passage of time regardless of the lighting fixture 1320 being in a powered-on or powered-off state.

In some cases, the lighting network may resume output according to profile 1300 after the profile has completed an 8-hour time span. In such cases, the lighting network may resume output based on the current time of the second (or additional) repetition of profile 1300. Alternatively, the lighting network may resume output based on a default state (e.g., not according to profile 1300), or based on a new repetition of profile 1300 (e.g., starting from the initial time point of profile 1300). In a shift working environment, this profile repetition may repeat a circadian strategy to promote wakefulness during each 8-hour shift (e.g., varying levels of high intensity blue lighting).

In some implementations, multiple circadian strategies or multiple associated profiles may be implemented by a BCS. For example, a hospital may have one or more lighting networks that serve patient rooms, and one or more additional lighting networks that serve hallways and nurses' stations. The lighting networks that serve patient rooms may produce light output based in part on a first profile intended to promote a regular sleeping schedule. The lighting networks that serve the nurses' stations may produce light output based in part on a second profile intended to promote wakefulness during a shift. In some cases, a lighting network may produce light output based in part on a combination of multiple profiles. In the above example of a hospital, the lighting networks that serve the hallways may produce light output based on a combination of the first and second profiles, such as to reduce sudden transitions between CI levels.

The profile may be dynamic and may be adjusted to reflect additional data received from the illuminated areas or spaces or from occupants within the areas or spaces. For example, sensors in a space may provide information that may be used to refine the profile. A daylight sensor may allow the profile to adjust for light entering through a window. Information collected from the occupants of the space may indicate that the profile needs to be adjusted to achieve a strategic CI for those particular occupants. For example, different occupants may experience a different CI when exposed to the same light output. Further, the distributed circadian model may provide input to refine the profile. For example, a common circadian strategy may be implemented throughout a building. Because each room within the building may include a different distributed circadian model, the profiles for each room may change based on the distributed circadian models to achieve the same circadian strategy in each room.

Data processing may occur with or without individual user feedback, including data or feedback from individuals who did not provide the data being processed for a particular user (i.e., crowd-sourced data). In an example, data processing may be performed for a particular first user on a particular day, but that user's provided data is incomplete for that day, perhaps because the user removed a wearable sensor for a portion of the day. In this example, data about the particular user's light levels during those hours could be provided by one or more other users wearing sensors in the same location, determined by geolocation data (e.g., from a mobile device). Additionally, data may be provided from fixed-location sensors in the building occupied by the particular user, such as public offices or retail buildings. Using the crowd-sourced data this way may provide data for a particular user that is not otherwise available.

Multiple occupants may have different desired benefits and may issue conflicting output requests to the BCS. To resolve any conflicts the BCS may provide a method for reconciling different user circadian impact goals into a single profile for a particular space. The reconciliation may be result in a profile that is based on an average of the output requests (e.g., an average of the profiles associated with the circadian impact goals). For example, the reconciliation may be the least disruptive to the largest number of users, or the reconciliation that accommodates the greatest need (e.g., an occupant's medical condition).

Figure 14:
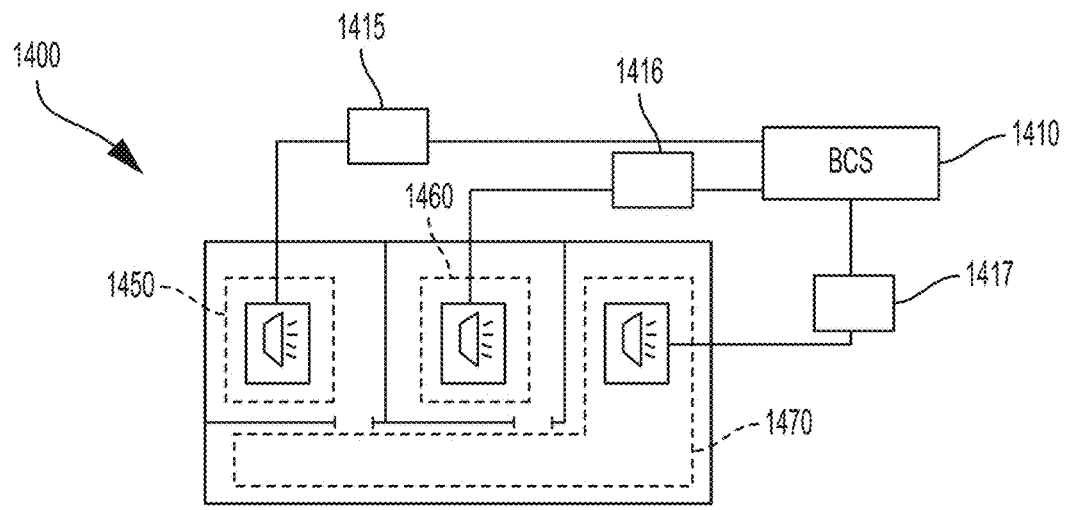
FIG. 14 depicts an exemplary system that includes a background circadian system capable of providing information to multiple lighting networks based on strategic profiles, according to certain examples of the present disclosure.

Circadian strategies and associated profiles may be implemented by one or more BCS's, including remotely located or distributed BCS's. FIG. 14 depicts an exemplary system 1400 that includes a BCS 1410 capable of providing information to multiple lighting networks 1450, 1460, and 1470 based on respective profiles tracking the circadian strategies. The BCS 1410 may include a computing device capable of communicating with multiple lighting networks, such as a personal computer, a server, or any other suitable computing device capable of providing multiple circadian strategies and/or associated profiles. The BCS 1410 may enable centralized control of multiple lighting networks 1450, 1460, and 1470. For example, the BCS 1410 may control a lighting system of an entire building from a centralized (or remote) location.

BCS 1410 may receive a selection of a circadian strategy, such as via input/output peripheral devices (e.g., keyboard, mouse), via a network connection, or via any other suitable technique. Based on the received selection, BCS 1410 may provide information describing a particular profile to a particular lighting network. For example, BCS 1410 may provide a first modifying factor 1415 to lighting network 1450, a second modifying factor 1416 to lighting network 1460, and a third modifying factor 1417 to lighting network 1470. Each of modifying factors 1415, 1416, and 1417 may describe a respective profile. For example, modifying factors 1415 and 1416 may each describe a first profile (or different time points in the first profile) associated with a first circadian strategy, and modifying factor 1417 may describe a second profile associated with a second circadian strategy.

Figure 15:
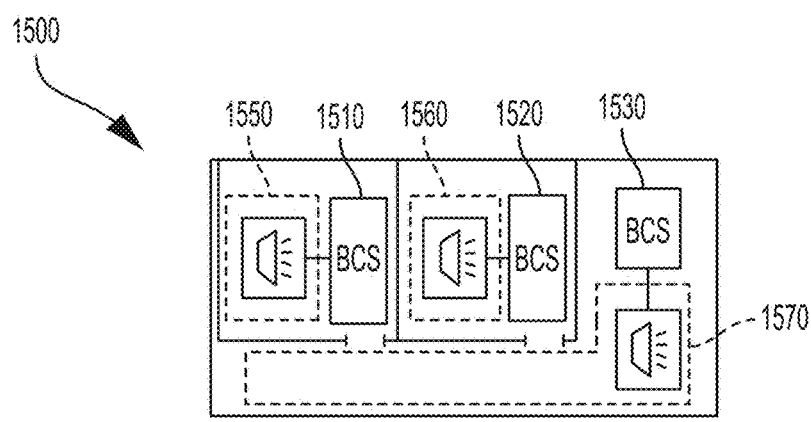
FIG. 15 depicts an exemplary system that includes multiple background circadian systems providing information to multiple lighting networks based on strategic profiles, according to certain examples of the present disclosure.

FIG. 15 depicts an exemplary system 1500 that includes multiple BCS 1510, 1520, and 1530, each capable of providing information to a respective one of lighting networks 1550, 1560, and 1570 based on a respective strategic profile. The BCS 1510, 1520, and 1530 may each include an electronic device capable of communicating with a given lighting network, such as a module including a programmed microprocessor, or any other suitable electronic device capable of providing a circadian strategy and/or associated profile.

In some cases, one or more of BCS 1510, 1520, and 1530 may include a single (e.g., pre-programmed) circadian strategy and/or associated profile. BCS 1510, 1520, and 1530 may each provide information describing the respective included profile to a respective lighting network. For example, BCS 1510 may provide to lighting network 1550 a first modifying factor describing the first profile included in BCS 1510. BCS 1520 may provide to lighting network 1560 a second modifying factor describing the second profile included in BCS 1520. BCS 1530 may provide to lighting network 1570 a third modifying factor describing the third profile included in BCS 1530. Each of the first, second, and third modifying factors provide input to the respective lighting networks 1550, 1560, and 1570 that represent the circadian strategy and/or associated profile for the lighting networks 1550, 1560, and 1570. In an example, the modifying factors may all provide the same input to the lighting networks 1550, 1560, and 1570. In another example, the first modifying factor and the second modifying factor may be the same due to the location of the lighting networks 1550 and 1560 in a similarly sized room, while the third modifying factor is different because the lighting network 1570 is in a room with a different size and shape.

In some implementations, one or more of BCS 1510, 1520, and 1530 may include multiple circadian strategies and/or associated profiles, selectable via an input device (e.g., on-board switch), via communication from a personal computing device (e.g., a mobile phone), or via any other suitable technique. Based on such selection, the BCS 1510, 1520, and 1530 may provide information describing the selected profile to the respective lighting network.

Figure 16:
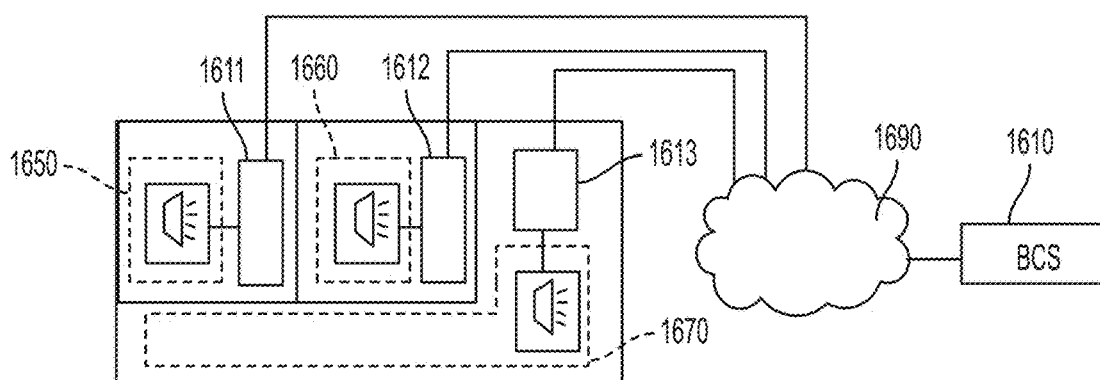
FIG. 16 depicts an exemplary system capable of transmitting a strategic profile from a remote background circadian system to one or more localized controllers, according to certain examples of the present disclosure.

FIG. 16 depicts an exemplary system 1600 capable of transmitting a respective strategic profile from remote BCS 1610 to one or more localized controllers 1611, 1612, and 1613. The respective profile may be transmitted via network 1690 (e.g., Internet, private network). The localized controllers 1611, 1612, and 1613 may each comprise an electronic device capable of communicating with a given lighting network and capable of communicating with a BCS via a network, such as a module including a programmed microprocessor and a network interface, or any other suitable electronic device capable of receiving and providing a profile.

BCS 1610 may receive a selection of one or more circadian strategies and/or associated profiles via a network connection, such as via user input to an interface (e.g., a browser, an application), or via any other suitable technique. The selected strategy may be associated with one or more of localized controllers 1611, 1612, and 1613 (e.g., by a localized controller identification). In some cases, the selection(s) may be associated with a user account. For example, a user may log in to a network-accessible account to provide a selection of a circadian strategy. In some cases, a user may subscribe to a strategy, such as via the user account, and BCS may provide to the localized controller a selected profile or strategy associated with the subscription.

Each of localized controllers 1611, 1612, and 1613 may receive respective information describing the selection for the respective localized controller. For example, the localized controllers may receive from BCS 1610 a respective profile associated with the strategy selected for that particular localized controller. In addition, the localized controllers may receive from BCS 1610 a respective indication of the selected circadian strategy. Responsive to receiving the indication, each respective device may access (e.g., local device storage, network-accessible location) a respective associated profile.

Based on the selected profile(s), each of localized controllers 1611, 1612, and 1613 may provide information describing the respective profile to a respective lighting network. For example, localized controller 1611 may provide to lighting network 1650 a first modifying factor describing the first profile selected for localized controller 1611. Localized controller 1612 may provide to lighting network 1660 a second modifying factor describing the second profile selected for localized controller 1612. Localized controller 1613 may provide to lighting network 1670 a third modifying factor describing the third profile selected for localized controller 1613.

Circadian Effect Light

In some situations, it may be desirable to increase a CI level in a space, while providing a minimum level of overall lighting in the space. A circadian effect light fixture ("effect light") may be used to increase a CI level within the context of the overall lighting. For example, the effect light may produce a circadian accent, and the circadian accent may include light that increases an amount of blue light perceived by a user. Additional lighting fixtures (or additional lighting elements included in the effect light) may produce task lighting for the work area. The combination of the circadian accent and the additional light may provide a level of overall lighting that is suitable for the task(s) performed at the work area and that provides a desired CI.

The effect light may produce the circadian accent via one or more lighting fixtures, or lighting element(s) within a lighting fixture(s). The effect light may produce the circadian accent by directing light towards a location within a space, such as by directing a higher-intensity light towards an occupant, providing colored light in a cove, projecting colored light on a wall, providing a wall with colored lights or with display devices that can produce color, or directing light towards an effect area, such as an area on the wall having a bright color. Generally, the effect light is configured so to project or reflect light in the plane of the eye of the occupant.

Figure 17A:
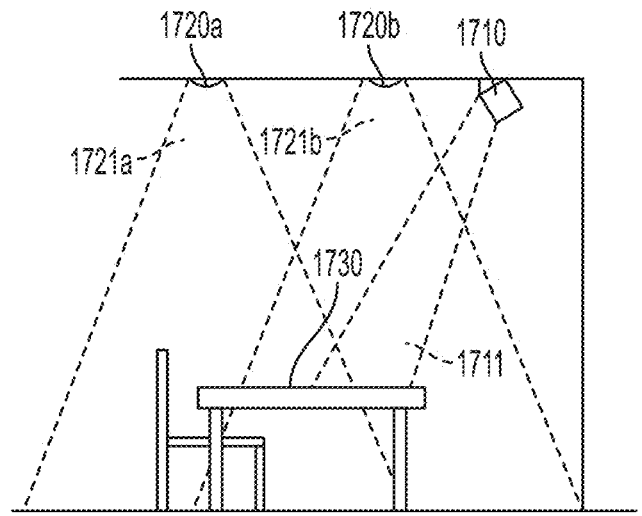
FIGS. 17a and 17b depict exemplary lighting systems capable of producing a circadian accent, according to certain examples of the present disclosure.
Figure 17B:
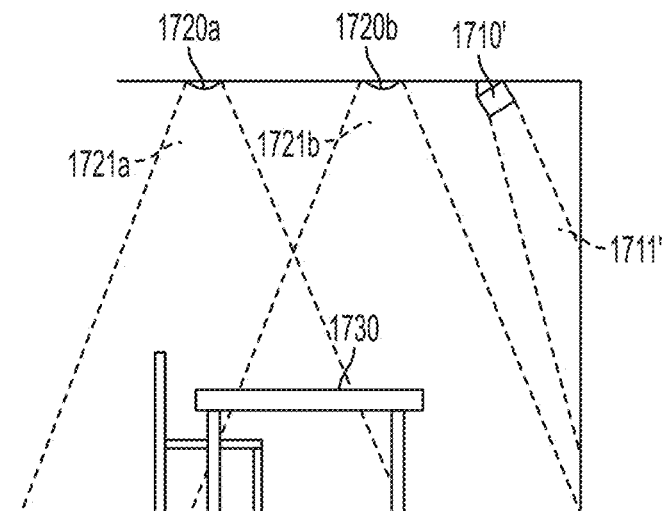

FIGS. 17*a* and 17*b* depict exemplary lighting systems capable of producing a circadian accent. In FIG. 17*a*, the lighting system includes lighting fixtures 1720 and an effect light 1710. The lighting system may provide light to a work area, such as work area 1730. Each of the lighting fixtures 1720*a* and 1720*b* may provide a respective light output 1721*a* and 1721*b*. The combination of light outputs 1721*a* and 1721*b* may provide, at the work area 1730, a first level of light having a first CI level. The first light level may be suitable for performing a task at the work area 1730. Tasks may include any activity performed for gain or enjoyment, such as professional activities, hobbies, exercise, chores, leisure activities, or other suitable activities. Work areas may be appropriate to the task(s), and may include a desk, floor, counter (e.g., kitchen, workbench), outdoor area, or other suitable areas.

Effect light 1710 may provide a light output 1711. Light output 1711 may include a circadian accent perceived by a person working at work area 1730. For example, the light output 1711 may include light having a particular CI level, such as produced light having a particular intensity, color, or color temperature. The combination of light outputs 1721*a*, 1721*b*, and 1711 may provide, to the person at the work area 1730, a second level of light having a second CI level. The second CI level may be greater (e.g., provide a larger amount of circadian impact) than the first CI level. The second level of light may be suitable for performing the task at the work area 1730, as well as providing a CI.

In some implementations, effect light 1710 may provide the circadian accent by adjusting the light output 1711. For example, effect light 1710 may change from a powered-off state to a powered-on state. In addition, effect light 1710 may adjust a level of light output, such as by modifying an intensity of light output 1711, or by modifying a color or color temperature of light output 1711. In some cases, effect light 1710 performs such adjustments at a particular position, such as depicted in FIG. 17*a*.

In some implementations, the lighting system depicted in FIG. 17 may produce a circadian accent by adjusting a position of an effect light. For example, effect light 1710' may be capable of adjusting its position (e.g., rotating, adjusting height, adjusting an internal reflective or absorptive component) such that lighting effect 1711' has a direction relative to the work area 1730. For example, effect light 1710' may adjust its position such that lighting effect 1711' is modified between a first direction (e.g., generally towards work area 1730) and a second direction (e.g., generally away from work area 1730). FIGS. 17*a* and 17*b* depict lighting effects 1711 and 1711' having exemplary directions towards and away from work area 1730, but other directions are possible.

In some implementations, multiple effect lights 1710 and 1710' may be positioned around the work area 1730. In such an example, each of the effect lights 1710 may be directed toward a different occupant positioned around the work area 1730. The effect lights 1710 may provide a different CI level to each of the occupants to correspond with the different CI profiles generated for each of the occupants. In an example, effect lights 1710 may each receive modifying factors that control the different CI levels of the effect lights 1710 to correspond with the different CI profiles. Similarly, in an open office space with separate cubicles, each of the multiple effect lights 1710 and 1710' may be directed into individual cubicle spaces to provide a desired CI level for each of the occupants of the open office space.

Figure 18A:
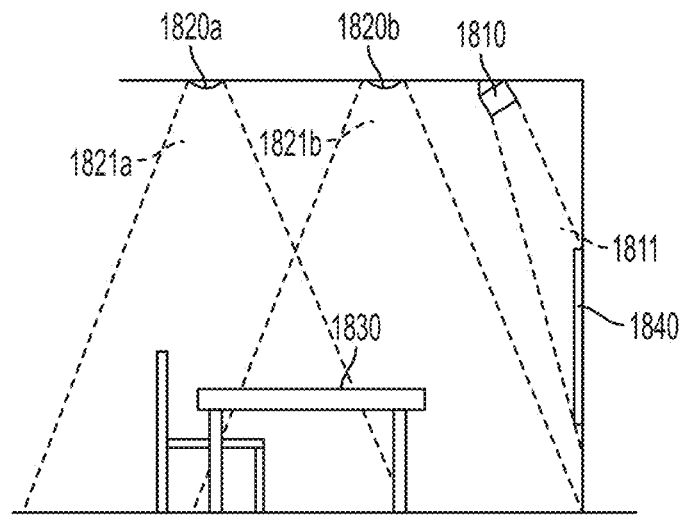
FIGS. 18a and 18b depict exemplary lighting systems capable of producing a circadian accent, according to certain examples of the present disclosure.
Figure 18B:
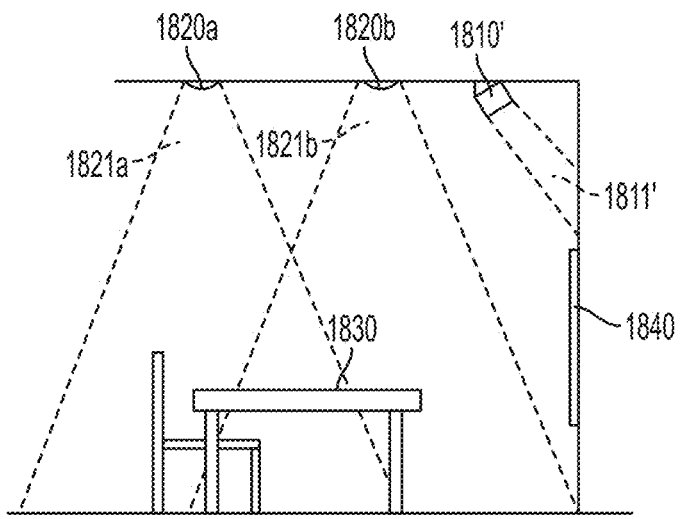

FIGS. 18*a* and 18*b* depict exemplary lighting systems capable of producing a circadian accent. In FIG. 18*a*, the lighting system includes lighting fixtures 1820 and an effect light 1810. The lighting system may provide light to a work area, such as work area 1830. Each of the lighting fixtures 1820*a* and 1820*b* may provide a respective light output 1821*a* and 1821*b*. The combination of light outputs 1821*a* and 1821*b* may provide, at the work area 1830, a first level of light having a first CI level, suitable for performing a task at the work area 1830.

Effect light 1810 may produce a light output 1811. Light output 1811 may provide a circadian accent perceived by a person located at work area 1830. For example, the light output 1811 may include white light (e.g., having a color temperature between about 2500K and about 6500K). The light output 1811 may be directed at an effect area 1840. Effect area 1840 may have an attribute capable of producing a circadian accent if light output 1811 is directed to the effect area. The attribute of the effect area 1840 may represent a color or reflective characteristics of the effect area 1840. For example, effect area 1840 may have a blue color that reflects blue spectral components of light output 1811. In addition, effect area 1840 may have one or more reflective components that reflect an intensity or a spectral component of light output 1811. Such attributes may produce a circadian accent, such as blue light or an intensity of light. In an example, the effect area 1840 is a painting, a sculpture, a photograph, or any other piece of artwork that includes a color profile that reflects a circadian accent to generate circadian impact lighting.

Effect area 1840 may be positioned such that at least some of the light output 1811 reflected from effect area 1840 may be perceived at work area 1830. The combination of light outputs 1821*a*, 1821*b*, and reflected light from 1811 may provide, at the work area 1830, a second level of light having a second CI level. A person at work area 1830 may perceive the circadian accent within the context of combined light outputs 1821*a*, 1821*b*, and reflected light from 1811. The second CI level may be greater (e.g., provide a larger amount of circadian stimulus) than the first CI level. The second level of light may be suitable for performing the task at the work area 1830, as well as providing a CI.

In some implementations, effect light 1810 may provide the circadian accent by adjusting the light output 1811. For example, effect light 1810 may change from a powered-off state to a powered-on state. In addition, effect light 1810 may adjust a level of light output, such as by modifying an intensity of light output 1811, or by modifying a color or color temperature of light output 1811. Effect area 1840 may reflect the modified light output 1811. In some cases, effect light 1810 performs such adjustments at a particular position, such as depicted in FIG. 18*a*.

In addition, the lighting systems depicted in FIGS. 18*a* and 18*b* may produce a circadian accent by adjusting a position of effect area 1840. For example, effect area 1840 may be capable of adjusting its position (e.g., horizontal or vertical adjustments, adjusting an internal reflective or absorptive component) such that lighting output 1811 is reflected in a direction relative to the work area 1830. Effect area 1840 may adjust its position such that reflected light is directed towards (or away from) work area 1830. In some cases, effect area 1840 may adjust its position such that light output 1811 is absorbed, or such that a particular spectral component of light output 1811 is absorbed. Such adjustments may result in an increase (or decrease) of CI levels perceived at work area 1830.

In addition, the lighting system depicted in FIG. 18*b* may produce a circadian accent by adjusting a position of an effect light. For example, effect light 1810' may be capable of adjusting its position (e.g., rotating, adjusting height, adjusting an internal reflective or absorptive component) such that lighting output 1811' has a direction relative to the effect area 1840. For example, effect light 1810' may adjust its position such that lighting output 1811' is modified between a first direction (e.g., generally towards effect area 1840) and a second direction (e.g., generally away from effect area 1840). FIGS. 18*a* and 18*b* depict lighting outputs 1811 and 1811' having exemplary directions towards and away from effect area 1840, but other directions are possible. In some cases, directing effect light 1810' away from effect area 1840 may result in lighting output 1811' being directed towards from an additional effect area having attributes capable of producing an additional circadian accent. A person at work area 1830 may perceive the circadian accent at the work surface 1830 within the context of combined light outputs 1821*a*, 1821*b*, and reflected light from 1811 or 1811'.

Another example of an exemplary lighting system capable of producing a circadian accent includes one or more display devices mounted to a wall or other area. The images displayed by the display devices may change over time to create a CI. For example, the display devices may display an image of a blue sky during the morning to increase blue spectrum and an image of a desert during the afternoon to lessen the amount of blue spectrum. In one or more examples, the displays of personal computers may also be controlled to create CI on an operator of the personal computer. For example, the CCT of the display of the personal computer may change throughout a day to track the operators CI profile.

Figure 19A:
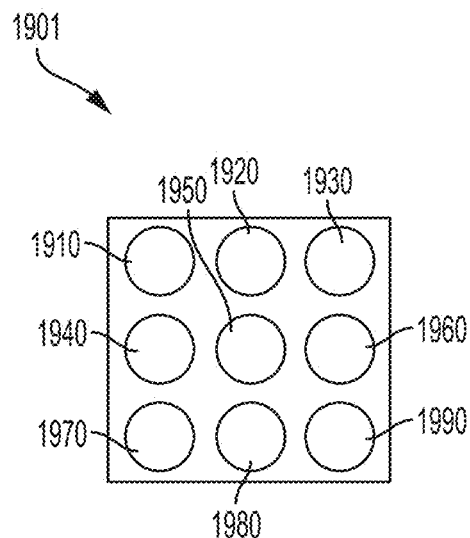
FIGS. 19a and 19b depict examples of lighting fixtures capable of producing a circadian accent using a set of included lighting elements, according to certain examples of the present disclosure.
Figure 19B:
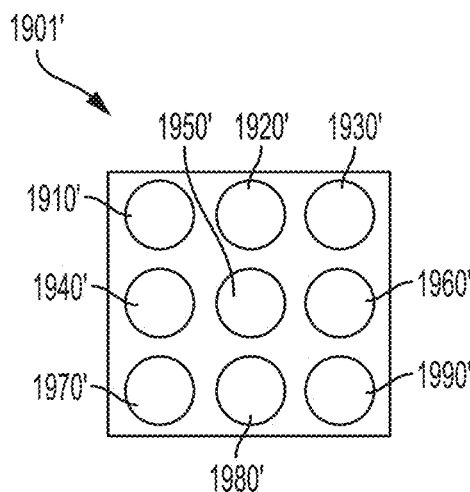

In some implementations, a lighting fixture having multiple lighting elements may be capable of producing a circadian accent. In addition, the circadian accent may be produced by a portion of the light output from the lighting fixture (e.g., from a subset of the multiple lighting elements). FIGS. 19*a* and 19*b* depict examples of lighting fixtures capable of producing a circadian accent using a set of included lighting elements. Each lighting element may be capable of producing light output having an intensity, color, color temperature or other suitable attribute. A lighting element may include one or more light-emitting diode (LED) emitters, incandescent emitters, fluorescent emitters, or other lighting devices. The lighting element may also include an entire fixture, a group of emitters, an organic light-emitting diode (OLED) emitter, an emitter with a color filter, a laser diode emitter, a quantum dot emitter, or any combination thereof.

In FIG. 19*a*, lighting fixture 1901 may include multiple lighting elements 1910, 1920, 1930, 1940, 1950, 1960, 1970, 1980, and 1990. Light fixture 1901 may produce an overall output based on the combined output of each lighting element 1910-1990. For example, each of the lighting elements 1910-1990 may produce a similar light output, such that the overall output of light fixture 1901 has a color temperature similar to the color temperatures of the lighting element outputs, and an intensity based on the combined intensities of the lighting element outputs. In addition, a first set of the lighting elements 1910-1990 may produce light output having a first color temperature and intensity, and a second set may produce light output having a second color temperature and intensity, such that the overall output of light fixture 1901 is based on the combined intensities and color temperatures of the first and second sets of lighting elements.

The lighting fixture may be capable of producing a circadian accent using one or more of the included lighting elements. The circadian accent may be produced within the context of the overall output of the lighting fixture. In FIG. 19*b*, lighting fixture 1901' produces an overall output based on the combined light output of the lighting elements 1910', 1920', 1930', 1940', 1950', 1960', 1970', 1980', and 1990'. A subset of the lighting elements and 1910'-1990' may produce light output providing a circadian accent. For example, lighting elements 1910', 1920', 1940', 1950', 1960', 1980', and 1990' may each produce a first level of light output. The first level of light output may be suitable for a person to perform a task. In an example, the first level of light output may be static when the lighting fixture 1901' outputs light (e.g., the circadian impact level of the first light output does not change). In addition, lighting elements 1930' and 1970' may each produce a second level of light output. The second level of light output may provide a circadian accent, such as light output having a CI level. Additionally, the second level of light output may be adjustable to track a CI profile of an occupant of a space lit by the lighting fixture 1901' (e.g., the circadian impact level of the second level of light output is adjustable).

The overall output of light fixture 1901' may be based on a combination of the first and second levels of light output. A person who is using the light output of light fixture 1901' (e.g., to perform a task) may perceive the circadian accent provided by lighting elements 1930' and 1970' within the context of the overall output of light fixture 1901'. The overall output of light fixture 1901' may provide light that is suitable to continue a task (e.g., without uncomfortable or irritating adjustments to color or intensity). Further, based on the adjustable circadian impact level of the second level of light, the combination of the first and second levels of light output is also adjustable.

In some implementations, a light fixture may produce the circadian accent by adjusting an attribute of one or more lighting elements. For example, a circadian accent may be produced by modifying a level of light output. The lighting elements 1930' and 1970' may each modify their level of light output, such as an intensity, color, or color temperature.

In addition, a circadian accent may be produced by modifying a position of one or more lighting elements. For example, the lighting elements 1930' and 1970' may modify a position, such as by rotating or adjusting an internal component. Adjusting the position of a particular lighting element within a light fixture may direct the light output of the lighting element away from the direction of the additional lighting elements' light output. For example, the position of lighting elements 1930' and 1970' may be adjusted such that their light output has a direction other than the direction of lighting elements 1910', 1920', 1940', 1950', 1960', 1980', and 1990'.

In addition, a circadian accent may be produced by modifying an additional attribute of one or more lighting elements. For example, lighting elements 1930' and 1970' may modify a filter, an aperture, a reflective or absorptive component, or other suitable attribute. The modified attribute may produce a circadian accent, such as by filtering one or more spectral components of a particular lighting element's light output, or by reflecting the light output away from the direction of the additional lighting elements.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multi-purpose microprocessor-based computer systems accessing stored software that programs or configures the computing system from a general purpose computing apparatus to a specialized computing apparatus implementing one or more examples of the present subject matter. Any suitable programming, scripting, or other type of language or combinations of languages may be used to implement the teachings contained herein in software to be used in programming or configuring a computing device.

Examples of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific examples thereof, it will be appreciated that those skilled in the art, upon attaining an understanding of the foregoing, may readily produce alterations to, variations of, and equivalents to such examples. Accordingly, it should be understood that the present disclosure has been presented for purposes of example rather than limitation, and does not preclude the inclusion of such modifications, variations, and/or additions to the present subject matter as would be readily apparent to one of ordinary skill in the art.

The invention claimed is:

1. A circadian effect light fixture, comprising:
   a controller configured to receive a first modifying factor from a background circadian system based on a circadian impact profile for a first space that specifies circadian impact values that vary over time, wherein the circadian impact profile for the first space is generated by the background circadian system in communication with the controller using a model comprising information on physical characteristics of the first space and based on information about tracked circadian impact value levels resulting from other light sources that are not part of the light fixture, wherein the first modifying factor varies over a range of time and comprises indications of an intensity value, a correlated color temperature value, and a color value for different points within the range of time;
   a first lighting element controlled by the controller to produce a first light output having a first intensity, a first correlated color temperature, and a first color value, wherein the first correlated color temperature and the first color value of the first lighting element are static while the first lighting element produces light output, wherein the first lighting element is configured to receive instructions from the controller to produce the first light output based at least in part on the first modifying factor; and
   a second lighting element controlled by the controller to produce a second light output having a second intensity, a second correlated color temperature, and a second color value, wherein the controller is configured to receive a second modifying factor from the background circadian system and the second lighting element is configured to receive instructions from the controller to produce the second light output based at least in part on the second modifying factor,
   wherein a combined light output of the first lighting element and the second lighting element tracks the circadian impact profile over the range of time, and wherein one or more of the second intensity, the second correlated color temperature, the second color value of the second light output are adjusted over the range of time based on the second modifying factor, and the first intensity of the first light output is adjusted over the range of time based on the first modifying factor, wherein the second modifying factor is based on the circadian impact profile and the static light output of the first lighting element,
   wherein the controller is further configured to receive user input from a user input device and wherein the controller is configured to cause the first lighting element or the second lighting element to produce light output according to a combination of the user input and the first or second modifying factor, respectively, and wherein when the user input from the user input device is completed, the controller is further configured to cause the first lighting element to produce light output according to the first modifying factor and to cause the second lighting element to produce the second light output according to the second modifying factor at a time of the circadian impact profile that is aligned with a current time.

2. The circadian effect light fixture of claim 1, comprising: a first background circadian system configured to generate the first modifying factor received by the controller.

3. The circadian effect light fixture of claim 1, wherein the second lighting element is configured to provide a circadian accent to the combined light output based on the second modifying factor to track the circadian impact profile over the range of time.

4. The circadian effect light fixture of claim 3, wherein the circadian accent comprises a change in the second correlated color temperature, a change in the second color value, or both.

5. The circadian effect light fixture of claim 1, wherein the first lighting element and the second lighting element each comprises light-emitting diode emitters, incandescent emitters, fluorescent emitters, organic light-emitting diode (OLED) emitters, color filtered emitters, laser diode emitters, quantum dot emitters, or any combination thereof.

6. A lighting system, comprising: at least one lighting fixture comprising: at least one first lighting element configured to produce a first light output to a location; and a first controller configured to control the first light output of the at least one first lighting element, wherein the first controller is configured to receive a first modifying factor from a background circadian system, wherein the first lighting element is configured to receive instructions from the first controller according to the first modifying factor, wherein the first light output comprises a static correlated color temperature and first color value when the first light output is at a selected intensity; and at least one circadian effect light fixture comprising: at least one second lighting element configured to produce a second light output to the location; and a second controller configured to control the second light output of the at least one second lighting element by adjusting a circadian impact level of the second light output based on a second modifying factor, wherein the second controller is configured to receive the second modifying factor from the background circadian system, wherein the first light output and the second light output provide a combined adjustable circadian impact level to the location based on the first and second modifying factors associated with a circadian impact profile for the location received by the lighting system, wherein the circadian impact profile specifies a circadian impact level of the location over a plurality of time periods, wherein the circadian impact profile for the location is generated by the background circadian system in communication with the first and second controller using a model comprising information on physical characteristics of the location and based on information about tracked circadian impact values levels resulting from other light sources that are not part of the lighting system, and wherein the first and second modifying factors vary over a range of time and comprises indications of circadian impact values for different points within the range of time, and the second modifying factor is based on the circadian impact profile and the static correlated color temperature and first color value of the first light output at the selected intensity, wherein the second controller is further configured to receive user input from a user input device and wherein the second controller is configured to cause the second lighting element to produce light output according to a combination of the user input and the second modifying factor, and wherein when the user input from the user input device is completed, the second controller is further configured to cause the second lighting element to produce light output according to the second modifying factor at a time of the circadian impact profile that is aligned with a current time.

7. The lighting system of claim 6, wherein the at least one second lighting element comprises a display of a computer device, a luminous fixture, or a television screen, and a correlated color temperature of the at least one second lighting element changes over the plurality of time periods based on the second modifying factor to produce the adjustable circadian impact level.

8. The lighting system of claim 6, wherein the combined adjustable circadian impact is configured to track the circadian impact profile of an occupant of the location.

9. The lighting system of claim 6, wherein the at least one second lighting element comprises a plurality of circadian effect lighting elements, wherein each of the plurality of circadian effect lighting elements is configured to produce light outputs at different adjustable circadian impact levels based on a plurality of second modifying factors associated with a plurality of circadian impact profiles.

10. The lighting system of claim 6, wherein the at least one second lighting element is adjustable between a first position and a second position such that the second light output is directed in a first direction associated with the first position and a second direction associated with the second position.

* * * * *